(12) United States Patent
Zhou et al.

(10) Patent No.: US 9,470,690 B2
(45) Date of Patent: Oct. 18, 2016

(54) HUMAN CANCER-RELATED GENE, ITS ENCODED PRODUCTS AND APPLICATIONS

(71) Applicant: Peking University, Beijing (CN)

(72) Inventors: Rouli Zhou, Beijing (CN); Genze Shao, Beijing (CN); Xinrong Liu, Beijing (CN); Qingyun Zhang, Beijing (CN); Jingan Rui, Beijing (CN); Ye Zhang, Beijing (CN); Yueying Jin, Beijing (CN); Ming Lin, Beijing (CN); Sha Zhang, Beijing (CN)

(73) Assignee: Peking University, Beijing (CN)

( * ) Notice: Subject to any disclaimer, the term of this patent is extended or adjusted under 35 U.S.C. 154(b) by 0 days.

(21) Appl. No.: 15/146,307

(22) Filed: May 4, 2016

(65) Prior Publication Data

US 2016/0238608 A1    Aug. 18, 2016

Related U.S. Application Data

(60) Continuation of application No. 13/019,297, filed on Feb. 1, 2011, which is a division of application No. 10/540,539, filed as application No. PCT/CN03/01109 on Dec. 24, 2003, now Pat. No. 7,910,711.

(30) Foreign Application Priority Data

Dec. 24, 2002 (CN) .................................. 02 1 58110
Apr. 21, 2003 (CN) .................................. 03 1 09786

(51) Int. Cl.
| | |
|---|---|
| G01N 33/50 | (2006.01) |
| G01N 33/53 | (2006.01) |
| G01N 33/574 | (2006.01) |
| C07K 14/705 | (2006.01) |

(52) U.S. Cl.
CPC ... G01N 33/57492 (2013.01); G01N 2333/705 (2013.01)

(58) Field of Classification Search
CPC ...................... G01N 33/5002; G01N 33/5005; G01N 33/5044; G01N 33/5067; G01N 33/53; C07K 14/47; C07K 14/4748; C07K 14/705; C07K 14/71
See application file for complete search history.

(56) References Cited

U.S. PATENT DOCUMENTS

| 6,465,620 B1 | 10/2002 | Boyle et al. |
| 2002/0172994 A1 | 11/2002 | Ruben et al. |
| 2005/0259483 A1 | 11/2005 | Nakamura et al. |

FOREIGN PATENT DOCUMENTS

| EP | 2230306 B1 | 5/2016 |
| JP | 2002 522018 A | 7/2002 |
| WO | 91/09045 A1 | 6/1991 |
| WO | 00/05367 A2 | 2/2000 |
| WO | 0056350 A2 | 9/2000 |
| WO | 01/12662 A2 | 2/2001 |
| WO | 01/53312 A1 | 7/2001 |
| WO | 02/059260 A1 | 8/2002 |
| WO | 02/071928 A2 | 9/2002 |
| WO | 2005/032495 A2 | 4/2005 |
| WO | 2005/044990 A2 | 5/2005 |

OTHER PUBLICATIONS

Database EMBL [Online] Mar. 1, 2001, "*Home sapiens* genomic DNA, chromosome 8q23, clone: KB1907C4." XP002591116 retrieved from EBI accession No. EMBL:AP003357 Database accession No. AP003357 Position 97598-97616; *abstract* (66 pages).
Database EMBL [Online] Jan. 29, 2001, "*Home sapiens* chromosome 8 clone RP11-53J21 map 8, Working Draft Sequence, 17 unordered pieces." XP002591117 retrieved from EBI accession No. EMBL: AC087826 Database accession No. AC087826 Position: 106198-106216; *abstract* (47 pages).
Database EMBL [Online] Oct. 29, 1999, "*Homo sapiens* chromosome 8 clone RP11-53J21, Working Draft Sequence, 17 unordered pieces." XP002591118 retrieved from EBI accession No. EMBL: AC012482 Database accession No. AC012482 Position: 45031-45050; *abstract; compound* (45 pages).
Database EPO Proteins [Online] Feb. 28, 2001, "Sequence 26 from Patent W0011262." XP002591120 retrieved from EBI accession No. EP0P:AX083484 Database accession No. AX083484 *abstract; compound* (1 page).
Office Action in corresponding Application EP 10153116.8 dated Jun. 4, 2014 (9 pages).
Office Action in corresponding Application EP 10153116.8 dated Nov. 24, 2014 (8 pages).
European Search Report in corresponding Application EP 10153116 dated Jul. 8, 2010 (4 pages).
Intention to Grant in corresponding Application EP 10153116.8 dated Oct. 5, 2015 (5 pages).
Decision to Grant in corresponding Application EP 10153116.8 dated Apr. 7, 2016 (2 pages).

(Continued)

*Primary Examiner* — Misook Yu
*Assistant Examiner* — Anne Holleran
(74) *Attorney, Agent, or Firm* — Hovey Williams LLP

(57) ABSTRACT

The invention discloses a human cancer-related gene, LAPTM4B, its encoded products and their applications thereof. This human cancer-related gene provided by this invention comprises one of the following nucleotide sequences: (1) SEQ ID No: 1, SEQ ID No: 2, SEQ ID No: 3, SEQ ID No: 6, or SEQ ID No: 8 in the sequence listings; (2) Polynucleotides that encode the protein sequences of SEQ ID No: 4, SEQ ID No: 5, or SEQ ID No: 7 in the sequence listings; (3) DNA sequences having above 90% homology with the DNA sequences specified by SEQ ID No: 1, SEQ ID No: 2, SEQ ID No: 3, SEQ ID No: 6, or SEQ ID No: 8 in the sequence listings, and these DNA sequences encode the proteins with the same or similar functions. This invention enables the developments of new anti-cancer approaches and new anti-cancer medicines. It would create a significant impact on human society.

5 Claims, 10 Drawing Sheets

(56) References Cited

OTHER PUBLICATIONS

Office Action in corresponding Application EP 10153116.8 dated Apr. 30, 2015 (8 pages).
Torimura, T., et al., Journal of Hepatology, 31:734-740, 1999.
Oh, Y.-K, et al., Advanced Drug Delivery Review, 61: 850-862, 2009.
Gen-Ze Shao et al., Molecular cloning and characterization of LAPTM4B, a novel gene upregulated in hepatocellular carcinoma, 2003, pp. 5060-5069.
Strausberg, et al., Mammalian Gene Collection (MGC) Program Team, Generation and initial analysis of more than 15,000 full-length humand and mouse cDNA sequences, Proceedings of the National Academy of Sciences of the U.S.A., Dec. 24, 2002, vol. 99 No. 26, pp. 16899-16903.
Kasper, Grit et al., The human LAPTM4b transcript is upregulated in various types of solid tumours and seems to play a dual functional role during tumor progression, Cancer Letters Aug. 8, 2004, vol. 224, No. 1, pp. 93-103.
Database Geneseq [Online] Oct. 22, 2001, Human Polypeptide SEQ ID No. 2720. XP002372228, retrieved from EBI accession No. GSP: AAM39575, Database accession No. AAM39575.
Database Geneseq [Online] Oct. 22, 2001, Human Polypeptide SEQ ID No. 2720. XP002372229, retrieved from EBI accession No. GSP: AAI58731, Database accession No. AAI58731.
Database EMBL [Online] Oct. 30, 2001, *Homo sapiens* Lysosomal Associated Transmembrane Protein 4 Beta, Variant 1 (LAPTM4B) mRNA, complete cds. XP002372230, retrieved from EBI accession No. EM_HUM: 4Y057051, Database accession No. AY057051.
Database EMBL [Online] Nov. 1, 2002, *Homo sapiens* Lysosomal Associated Protein Transmembrane 4 Beta, mRNA (cDNA clone MGC:43257 Image:5264567), complete cds. XP002372231, retrieved from EBI accession No. EM_HUM: BC038117, Database accession No. BC038117.
Database Geneseq [Online] Feb. 25, 2003, Human Protein SEQ ID No. 364. XP002372232, retrieved from EBI accession No. GSP: ABP64704, Database accession No. ABP64704.
Database Geneseq [Online] Mar. 1, 2001, Human Genomic DNA, chromosome 8q23, cline: KB1907C4. XP002372233, retrieved from EBI accession No. EM_HUM:AP003357, Database accession No. AP003357.
Arvanitis et al. "Conditional transgeneic models define how MYC initiates and maintains tumorigenesis" Seminars in Cancer Biology, 16 (2006): 313-317.
Cheng et al. Relationship between LAPTM4B gene polymorphism and susceptibility of colorectal and esophageal cancers, Ann. Oncol., 2008, 19(3): 527-532.
Deng et al. "Relationship between LAPTM4B gene polymorphism and susceptibility of lung cancer", Beijing Da Xue Bao, 2005, 37(3):302-305. Abstract.
Hanahan et al. "The hallmarks of cancer." Cell, 2000, 100(1): 57-70.
He et al "Effect of the novel gene, LAPTM4B, highly expression in hepatocellular carcinoma on cell proliferation and tumorgenesis of NH3T3 cells" J. Peking University (Health Sciences), 2003, 35(4):348-352.
Liu et al. Structure analysis and expressions of a novel tetratransmembrane protein, lysosomaassocaited protein transmembrane 4 beta associated with hepatocellular carcinoma, World J. Gastroenterol, 2004, 10(11): 1555-1559.
Liu et al. "Relationship between LAPTM4B gene polymorphism and susceptibility of gastric cancer" Ann. Oncol., 2007. 18(2): 311-316.
Pelengaris et al. "c-MYC: more than just a matter of life and death", Nt. Rev. Cancer, 2002, 2(1):764-776.
Peng et al. "Express of lysosome-associated protein transmembrane 4B-35 in cancer and its correlation with the differentiation status of hepatocellular carcinoma." World J. Gastroenterol. 2005, 11(18): 2704-2708.
Shachaf et al. "MYC inactivation uncovers pluripotent differentation and tumour doarmancy in hepatocellular cancer" Nature, 2004, 431(7012): 1112-1117.
Yang et al. "LAPTM4B overexpression is an independent prognostic marker in ovarian carcinoma", Oncology Reports, Jul. 2008, accepted.
Zhou et al. "Overexpression of LAPTM4B-35 closely correlated with clinicopathological features and post-resectional survival of gallbladder carcinoma". European Journal of Cancer, 43 (4): 809-815.
Zhou et al. Expression of LAPTM4B-35: A novel marker of progression, invasiveness and poor prognosis of extrahepatic cholangiocarcinoma, Cancer Letter, 264(2): 209-217.
Zhou et al. "LAPTM4B, a hepatocellular carcinoma-associated novel proto-oncogene", Falk Symposium 150, Berlin, 2005. 10. Abstract p. 121 and poster prized by the conference.
EBI Accession No. EM_HUM: AY057051, *Homo sapiens* putative integral membrane protein mRNA, complete cds.
Liu et al., "Biological function of a novel gene overexpressed in human hepatocellular carcinoma", Chinese Medical Journal, vol. 13, No. 10, p. 881-885 (2000).
Accession No. AY057051 NCBI. http://www.ncbi.nlm.nih.gov/nuccore/AY057051 as retrieved Apr. 15, 2010.
Weimann, et al. Genome Research, 2001. vol. 11, pp. 422-435.
Acland, Dixon, Peters and Dickson. Subcellular fate of the Int-2 oncoprotein is determined by choice of Initiation codon. Nature, 1990. vol. 343, pp. 662-665.
Zhou et al. LAPTM4B, A Novel Cancer Target (II), The 3rd International Congress of Cancer progression, Baltimore, 2006, Abstract, p. 102-103 and poster.
Zhou et al. LAPTM4B plays critical roles in tumerigenesis of human cells by activating several signaling pathways, The 5th Asian-Pacific Organization for Cell Biology Congress, 2006, Beijing Abstract, p. 77, oral presentation.
Zhou et al. LAPTM4B activates signaling pathways of cell survival and proliferation as an organizing platform for signal molecules and plays critical roles in malignant transformation, The 9th Conference of Chinese Society for Cell Biology, Abstract p. 52, 2007, Guangzhou, oral presentation.
Pennica et al. Proc. Natl. Acad. Sci. USA, 95:14717-14722, 1998.
Konopka et al. Proc. Natl. Acad. Sci. USA, 83:4049-4052, 1986.
Chen et al. Molecular and Cellular Proteomics 1:304-313, 2002.
Hu et al. Journal of Proteome Research 2(4):405-412, 203.
Haynes et al. Electrophoresis 19:1862-1871, 1998.
Gygi et al. Mol. Cell. Biol. 19:1720-1730, 1999.
Lian et al. Blood 98:513-524, 2001.
Fessler et al. The Journal of Biological Chemistry. 277:31291-31302, 2002.
Hanash S. Nature Reviews, Applied Proteomics Collection, pp. 9-14, Mar. 2005.
Labaer J. Nature Biotechnology 21:976-977, 2003.
Lewin, B. ed. Genes IV, Oxford University Press, 1990. p. 810.
Skolnick, J. et al. From genes to protein structure and function: novel applications of computational approaches in the genomic era. Trends in Biotechnology, 2000. vol. 18, pp. 34-39.
Burgess, W.H. et al. Possible dissociation of the heparin-binding (acidic fibroblast) growth factor-1 from its receptor binding activities by site-directed mutagenesis of a single lysine residue. Journal of Cell Biology, 1990. vol. 111, pp. 2129-2138.
Lazar, E., et al. Transforming growth factor a: mutation of aspartic acid 47 and leucine 48 results in different biological activites. Molecular and Cellular Biology, 1988. vol. 8, pp. 1247-1252.
Schwartz, G.P. et al. A superactive insulin: [B10-Aspartic acid]insulin (human). Proceedings of the National Academy of Sciences, 1987. vol. 84, pp. 6408-6411.
Lin, M.C. et al. Structure-function relationships in glucagon: properties of highly purified Des-His1-Monoiodo-, and [Des-Asn28, Thr29](homoserine lactone27)glucagon. Biochemistry, 1975. vol. 14, pp. 1559-1563.
Genbank accession No. AAP14034, submitted Aug. 11, 2003.
Genbank accession No. AA084265, submitted Apr. 21, 2003.
Genbank accession No. AY198226, submitted Aug. 11, 2003.

FIG. 1-A
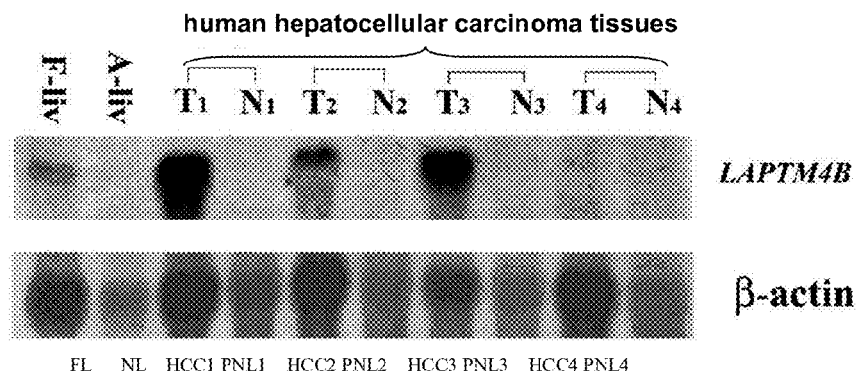
FIG. 1-B
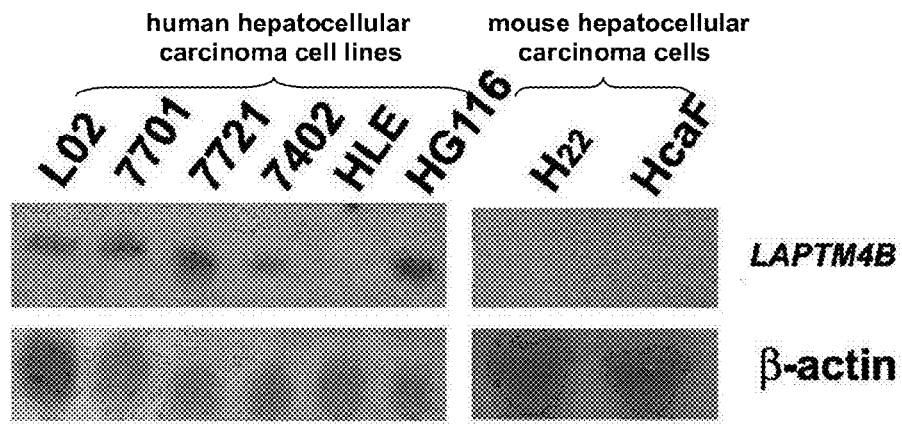
FIG. 1-C
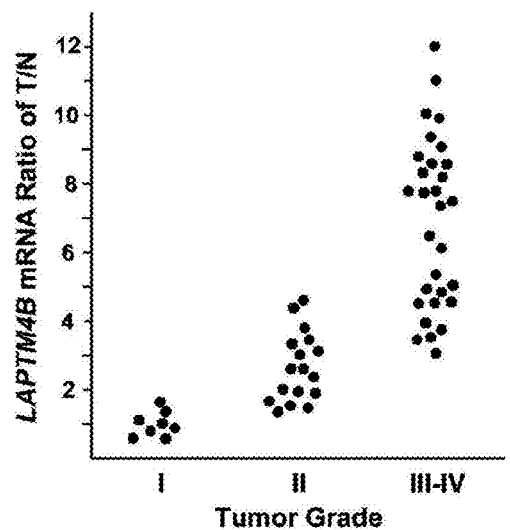

FIG. 2-A
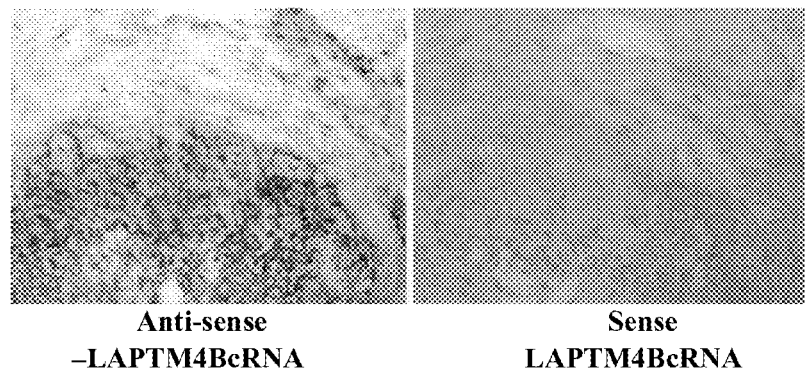
Anti-sense −LAPTM4BcRNA    Sense LAPTM4BcRNA
FIG. 2-B
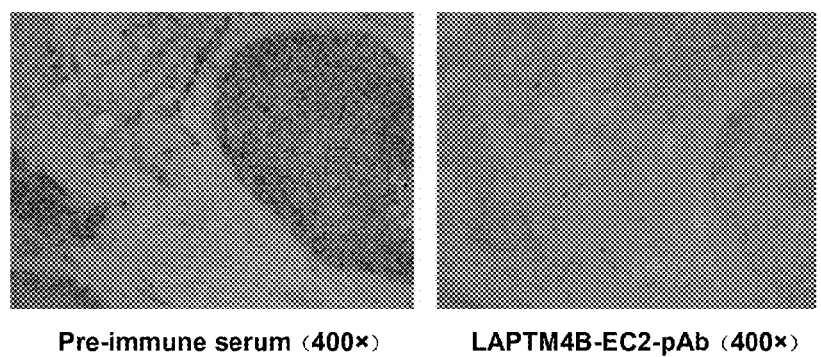
Pre-immune serum (400×)    LAPTM4B-EC2-pAb (400×)
FIG. 2-C
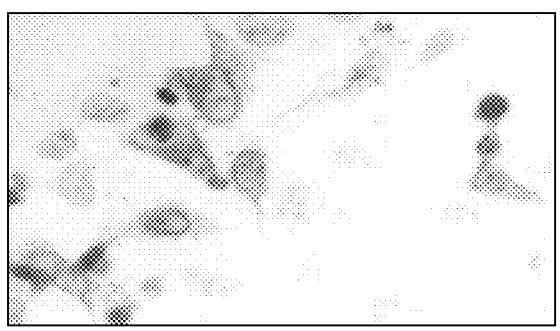

FIG. 9
A
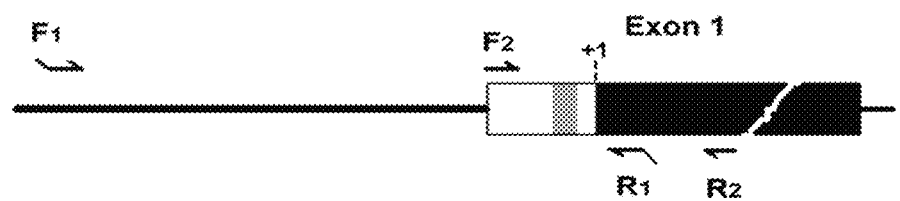
B
TTACTCACCGGGTGCTTGGAGCTCCAGCAGCTGGCTGGAGCCCGCGA
SEQ ID No. 19
*LAPTM4B *1*
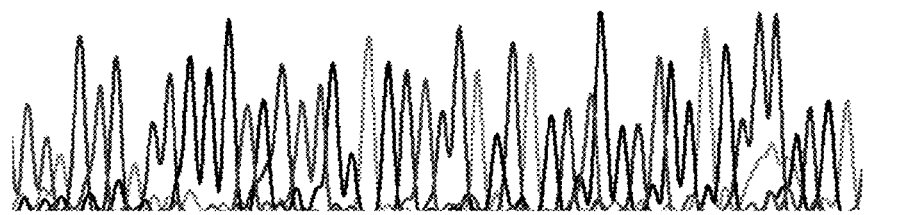
GGGTGCTTGGAGCTCCAGCAGCTGCTTGGAGCTCCAGCAGCTGGCT
SEQ ID No. 20
*LAPTM4B *2*
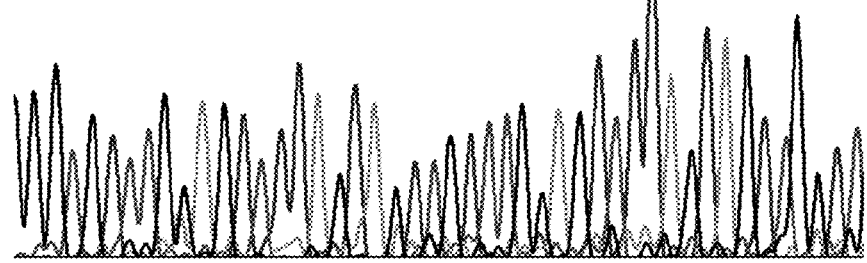

FIG. 12
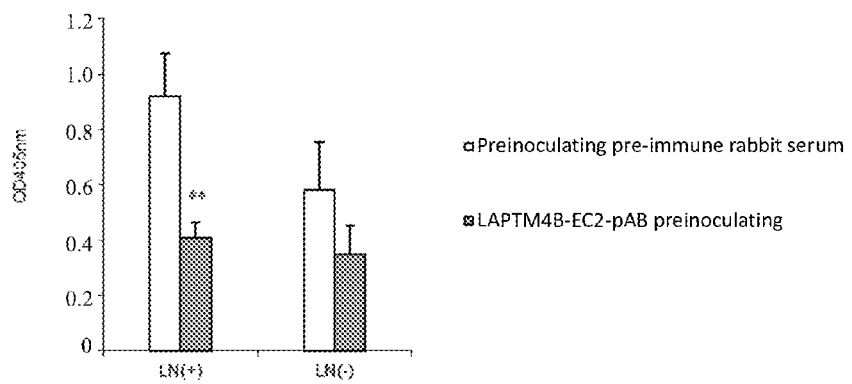
**P < 0.01 LAPTM4B-EC2-pAb vs. pre-immune rabbit
FIG. 13-A
FIG. 13-B
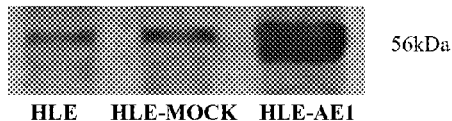
FIG. 13-C
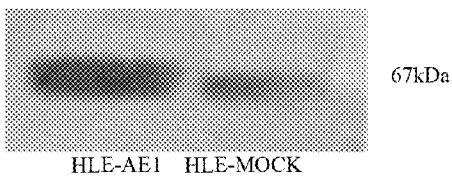
FIG. 13-D

FIG. 13-E
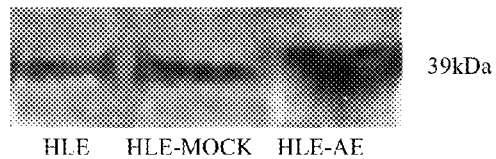
FIG. 14-A
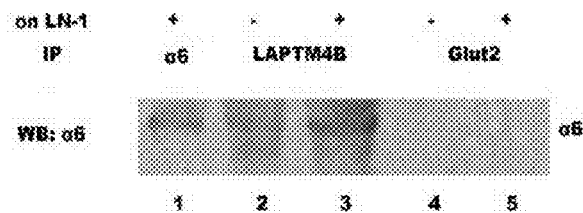
FIG. 14-B
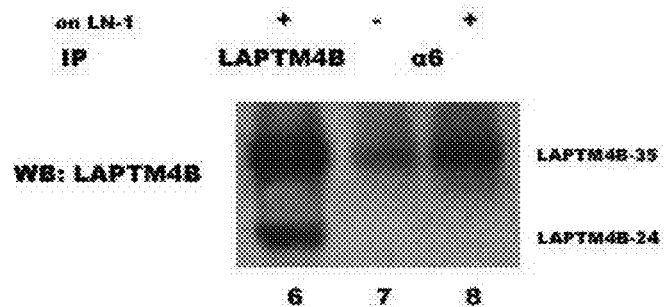
FIG. 14-C
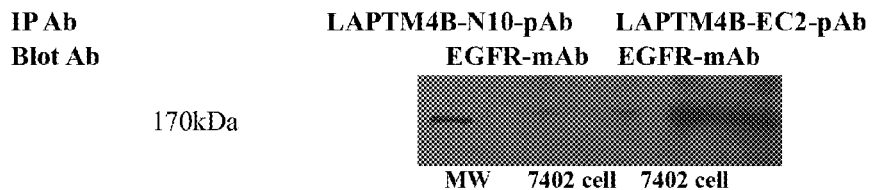
FIG. 15-A
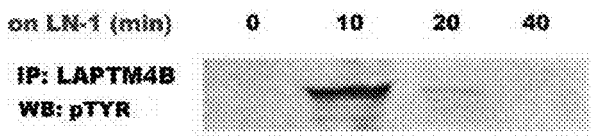
FIG. 15-B
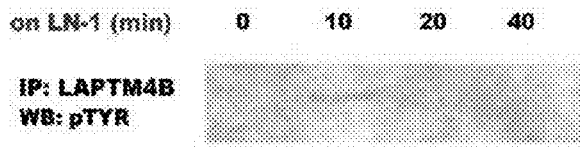

FIG. 15-C
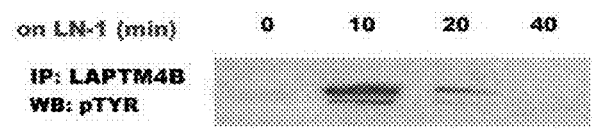
FIG. 16-A
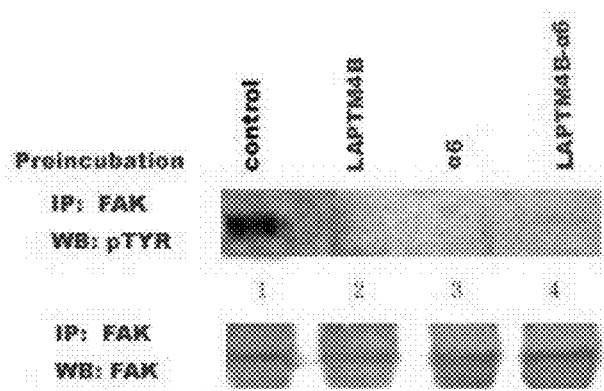
FIG. 16-B
LAPTM4B-EC2-pAb preincubation     –    +
IP: MAPK
WB: pTYR
IP: MAPK
WB: MAPK
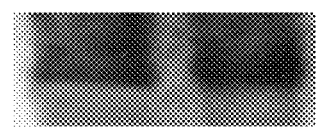

HUMAN CANCER-RELATED GENE, ITS ENCODED PRODUCTS AND APPLICATIONS

CROSS REFERENCE TO RELATED APPLICATIONS

This application is a continuation of U.S. Ser. No. 13/019,297, filed Feb. 1, 2011, incorporated by reference herein in its entirety, which is a divisional of U.S. Ser. No. 10/540,539, filed Oct. 4, 2006, now U.S. Pat. No. 7,910,711, which is a national stage of PCT/CN2003/01109, filed Dec. 24, 2003, which claims the priority benefit of Chinese Application No. 02158110.X, filed Dec. 24, 2002, and Chinese Application No. 03109786.3, filed Apr. 21, 2003.

SEQUENCE LISTING

The following application contains a sequence listing in computer readable format (CRF), submitted as a text file in ASCII format entitled "SequenceListing," created on May 3, 2016, as 22 KB. The content of the CRF is hereby incorporated by reference.

FIELD OF THE INVENTION

The present invention relates to a human cancer-related gene, its encoded products and their applications in genetic engineering and protein engineering areas, as well as in medical diagnosis and treatment.

BACKGROUND OF THE INVENTION

Cancer is the major health problem threatening human lives. Hepatocellular carcinoma (HCC) is one of the most serious among cancer diseases. It is reported that the new cases of primary hepatocellular carcinoma exceeds over one million worldwide each year. 70% of the new cases occur in Asia, and about 40-45% of the worldwide new cases occur in China. The total number of new hepatocellular carcinoma cases every year in China is about 450,000, and the number is increasing, especially in those between ages 20-60. The high incidence, difficulty in early diagnosis, fast growing rate, high reoccurrence, and the high mortality rate make HCC a most malignant cancer. Most HCC patients have already progressed to the intermediate stage or late stage when diagnosed, and they can only survive for 3-6 months if without a proper treatment.

To elucidate the mechanism underlying cancerogenesis would help for cancer prevention, diagnosis and treatment. Early diagnosis is crucial for raising the curative rate and reducing the mortality. Currently used HCC-diagnostic marker, the serum AFP, has 30% of negative results in HCC patients, while some benign liver disease can cause a significant increase of AFP level in serum, creating some difficulty in differential diagnosis. It has been found that the hepatocarcinogenesis is related to individual hereditary susceptibility. Individuals with different genetic backgrounds possess different handling capability toward environmental carcinogens. This leads to different risk of suffering from cancer for individuals. It is the various genotypes and the genetic diversity that cause the different genetic susceptibility for cancerogenesis.

Cancer is essentially a cellular hereditary disease. Although a great number of cancer-related genes have been discovered, the mechanisms of the cancerogenesis and the development remain to be elucidated. The known oncogenes can be divided into five categories according to the cellular localization and function of their encoded proteins: I. genes that encode growth factors, including sis, int-2, hst, fgf-5; II. genes that encode growth factor receptors, including erbB, erbB-2, fins, met, ros, and others; III. genes that encode signal transduction molecules in cytoplasm, including abl, src, ras, raf, yes, fgr, fes, lck, mos, and others; IV. genes that encode regulatory molecules for cell proliferation and apoptosis, including bcl-1, bcl-2 and others; and V. genes that encode the nuclear DNA-binding proteins (transcription factors), such as myc, myb, fos, jun, B-lym, ski, ets, rel and others. It has been demonstrated that ras, src, myc, met and p53 etc. are the genes closely associated with HCC.

SUMMARY OF THE INVENTION

This invention provides a novel human cancer-related gene and its encoded products.

This novel human cancer-related gene provided by this invention is designated as LAPTM4B. It comprises one of the following nucleotide sequences:

1. The human cancer-related gene comprises one of the following nucleotide sequences:
   1). SEQ ID No: 1, SEQ ID No: 2, SEQ ID No: 3 or SEQ ID No: 6 in the sequence listings;
   2). Polynucleotides that encode the protein sequences of SEQ ID No: 4, SEQ ID No: 5, or SEQ ID No: 7 in the sequence listings;
   3). DNA sequences having more than 90% homology with the DNA sequences defined by SEQ ID No: 1, SEQ ID No: 2, SEQ ID No: 3 or SEQ ID No: 6 in the sequence listings. These DNA sequences can encode proteins having the same or similar functions.

SEQ ID No: 1 in the sequence listings mentioned above contains 954 bases. It is an intact open reading frame. SEQ ID No: 1 has two starting sites, one is the base at 1-3 site at 5' terminal, and another is the base at 274-276 site at 5' terminal. Two complete cDNAs in SEQ ID No: 1 have two alternative tailing signals. When 5' terminal in SEQ ID No: 1 is extended outward by 85 bases, and 3' terminal is extended outward by 401 bases, SEQ ID No: 2 in the sequence listings is obtained. This gene contains 1440 bases. When 5' terminal in SEQ ID No: 1 is extended outward by 85 bases, and 3' terminal is extended outward 1130 bases, SEQ ID No: 3 in the sequence listings is obtained. This gene is consisted of 2169 bases. LAPTM4B gene localizes on chromosome 8q22.1.

In the sequence listings, SEQ ID No: 6 is the allelic gene of SEQ ID No: 1, consisting of 2264 bases. Its open reading frame starts from 17 to 1129 base. This sequence contains two tandemly arranged 19 bp DNA segments, the sequence of which is gcttgg agctccagca gct. These 19 bp DNA segments localized in nt 124-nt 161 in SEQ ID No: 6.

The human cancer related LAPTM4B protein possesses the amino acid sequence of 4, and/or 5, and/or 7. Or it consists of the sequence 4, and/or the sequence 5, and/or the sequence 7 after one or several amino acid residues are replaced, deleted, or added. However, the above altered sequence 4, and/or the sequence 5, and/or the sequence 7 still have the same or similar activity to the unchanged sequence 4, and/or the sequence 5, and/or the sequence 7.

Sequence 4 in the sequence listings consists of 317 amino acid residues encoded by the whole sequence of SEQ ID No: 1. Its molecular mass is 35 kDa and the putative isoelectric point is 9.05. Sequence 5 in the sequence listings contains 226 amino acid residues encoded by the segment of bases from 274th to 954th in the SEQ ID No: 1. Its molecular mass is 24 kDa, and the putative isoelectric point is 4.65. The sequence 7 in the sequence listings is a protein containing 370 amino acid residues.

LAPTM4B gene is widely expressed at different levels in sixteen normal tissues. Its transcriptive expression is very high in testis, cardiac muscle, and skeletal muscle, moderate in ovary, kidney, and pancreas, low in liver, spleen, small intestine, large intestine, and thymus, and is very low in lung and peripheral blood cells. In eight fetal tissues, the expression is high in heart, skeletal muscle, and kidney. In fetal livers, it is slightly higher than that in adult livers. However, its expression in some cancerous tissues is significantly upregulated. For instance, the Northern Blot analysis indicates that the transcription level in 87.3% (48/55) human hepatocellular carcinoma tissues is significantly higher than that in fetal livers and normal livers (FIG. 1-A). In situ hybridization (FIG. 2-A), immunohistochemistry (FIG. 2-B), and immunocytochemistry (FIG. 2-C) also indicate that LAPTM4B gene expression is especially high in hepatocellular carcinoma tissues, while its expression is relatively low in paired non-cancerous liver tissues (FIGS. 2-A and 2-B). Among the five cell lines from hepatoma tissues tested, all except for HLE, SMMC-7721, QGY-7701, BEL7402 and HG116 are expressed highly (FIG. 1-B and FIG. 2-C). It is important that highly over expressed protein product in hepatocellular carcinoma tissue and hepatocellular carcinoma cell line is mainly SEQ ID No: 4 LAPTM4B-35, while SEQ ID No: 5 LAPTM4B-24 only shows a slightly up regulation in its expression level. This results in a remarkable increase in the ratio of LAPTM4B-35 to LAPTM4B-24 proteins in the hepatocellular carcinoma tissue (FIG. 2-B). Although the expressions of LAPTM4B-35 and LAPTM4B-24 are slightly increased in the paired non-cancerous tissue, their ratio is the same as that in the normal liver (See Table 1). This is probably a precancerous sign of hepatocellular carcinoma. In addition, the expression levels of mRNA and the protein of LAPTM4B gene is negatively correlated with the differentiation of the hepatocellular carcinoma tissue. The hepatocellular carcinoma tissues in low differentiation are expressed highly, while the ones in high differentiation are expressed relatively low (FIG. 1-C). The Western Blot and the immunohistochemical method are used to determine the relationship of LAPTM4B gene with other cancers. The results indicate that LAPTM4B-35 protein expression is up regulated in some epithelium derived cancerous tissues and cell lines, such as stomach cancer, breast cancer, highly metastatic human lung cancer, and prostate cancer (FIG. 11). Moreover, in syngeneic human lung cancer and prostate cancer cell lines, LAPTM4B-35 expression is greatly up regulated in cells of high metastasis potential compared with those of low metastasis potential. But in cell lines of human melanoma, either from in situ or metastatic cancer, it is not clearly expressed. Although LAPTM4B-35 is expressed at a low level in liver tissues of adult rats and mice, its expression is not obviously up regulated in either mouse ascetically grown hepatocellular carcinoma or in the regenerated rat liver under a normal proliferation status.

TABLE 1

Expression ratio of LAPTM4B-35 to LAPTM4B-24 in hepatocellular carcinoma tissue, paired non-cancerous liver tissue and normal liver tissue

|  | HCC | PNL | NL |
| --- | --- | --- | --- |
| LAPTM4B-35 | 13.32 ± 1.98 | 4.58 ± 1.31 | 2.78 ± 0.11 |
| LAPTM4B-24 | 3.59 ± 1.78 | 1.76 ± 1.24 | 1.00 ± 0.02 |
| LAPTM4B-35/ LAPTM4B-24 (Ratio) | 3.71 | 2.60 | 2.78 |

P < 0.01 HCC vs. PNL and NL

LAPTM4B proteins in SEQ ID No: 4, SEQ ID No: 5 and SEQ ID No: 7 have four fragments of membrane-spanning sequences, one N-glycosylation site, a typical lysosome and endosome targeting signals in the cytoplasmic region. They all belong to the protein superfamily of the tetratransmembrane proteins. However, they have various number of phosphorylation sites. The experiment shows that SEQ ID No: 4 LAPTM4B-35 can form a complex in plasma membrane with the integrin α6β1 (Single specific receptor of laminin in the extracellular matrix) and the epidermal growth factor receptor (EGFR) (FIGS. 14-A, B, and C). This complex is colocalized in cell plasma membrane. It is possible that LAPTM4B-35 may integrate in the plasma membrane the proliferation signals from both extracellular matrix and the growth factor. This can further elucidate molecular mechanism of the anchorage-dependent cell growth of normal eukaryotic cells, i.e. the eukaryotic cell growth needs not only the stimulating signal from the growth factor, but also a definite stimulating signal from extracellular matrix. It represents a break through in understanding the regulation mechanism of the cell proliferation. Experiments demonstrate that tyrosine group ($Tyr_{285}$) in the cytoplasmic region of LAPTM4B protein C terminal can be phosphorylated (FIG. 15-A). When the cell is attaching onto the laminin substrate, its phosphorylation is increased sharply (FIG. 15-A) and can be completely inhibited by LAPTM4B-EC2-pAb antibody (FIG. 15-B), but the non-correlated antibody does not show any inhibitory effect (FIG. 15-C). After the phosphorylation, $Tyr_{285}$ forms a site to bind with the SH2 domain of intracellular signal molecules. In the meantime, N terminal and C terminal sequences of LAPTM4B contain Pro-rich domains and binding sites of the typical SH3 I domain. The above results indicate that SEQ ID No: 4 LAPTM4B-35 protein may be an important docking protein for signal transduction, or an organizer of the special microdomain in the plasma membrane. It can recruit related signal molecules from both inside and outside of the cells to complete the signal transduction for cell proliferation, differentiation, and apoptosis. Experimental results show that the transfection of mouse NIH3T3 cells and HLE human hepatocellular carcinoma cells by cDNA in SEQ ID No: 4 produces stable transfected and LAPTM4B-35 over expressed NIH3T3-AE and HLE-AE cell lines. The growth curves (FIG. 4), the incorporation of 3H-TdR (FIG. 5), and the cell numbers in S phase of cell cycle (FIG. 6) all demonstrate that the rate of cell proliferation is greatly increased. Moreover, the proliferation of transfected cells shows less dependence on the growth factor in serum, and the transfected cells can form large colonies in soft agar. Inoculation of NIH mouse with NIH3T3-AE cells can form a moderate malignant fibrosarcoma (FIG. 7), indicating the over expression of LAPTM4B-35 induces out of control of the cell proliferation. Also migration capability of the HLE-AE cells is strengthened and its capability to invade the Matrigel is remarkably enhanced, indicating that the over expression of LAPTM4B-35 accelerates the development of cell malignant phenotype. On the contrary, the cDNA of SEQ ID No: 5 (An encoding sequence where 91 amino acids in the N terminal of LAPTM4B-35 is truncated) transfected mouse BHK, NIH3T3, and HLE hepatocellular carcinoma cell lines cannot survive for a long time. The result shows that the 91 amino acid sequence on the N terminal of SEQ ID No: 4 LAPTM4B-35 protein play a crucial role in regulating cell proliferation. LAPTM4B-35 protein and LAPTM4B-24 protein have reciprocal, antagonistical functions in cell proliferation and survival. The overexpression of LAPTM4B-35 accelerates cellular malignant transformation, while the overexpression of LAPTM4B-24 facilitates the cell death.

Their expression equilibration and regulation are pivotal to the carcinogenesis and progression of malignant cancer. LAPTM4B gene may belong to the proto-oncogene family. In cancer treatment, inhibiting SEQ ID No: 4 LAPTM4B-35 expression and strengthening SEQ ID No: 5 LAPTM4B-24 expression may suppress the growth of hepatocellular carcinoma and reverse its malignant phenotype or progressively slow down its development. Furthermore, the overexpression of LAPTM4B-35 also promotes upregulation of the cell cycle regulators, such as cyclin D1 (FIG. 13-A) and cyclin E (FIG. 13-B), and also the over expression of some proto-oncogenes, such as c-Myc (FIG. 13-C), c-Jun (FIG. 13-D), and c-Fos (FIG. 13-E) etc.

The monoclonal and polyclonal antibodies for SEQ ID No: 4 LAPTM4B-35 protein epitopes, such as polyclonal LAPTM4B-EC2$_{232-241}$-pAb for SEQ ID No: 4 LAPTM4B-35 in the secondary extracellular region, polyclonal antibodies (LAPTM4B-N$_{1-99}$-pAb and LAPTM4B-N$_{28-37}$-pAb) for SEQ ID No: 4 LAPTM4B-35 N terminal sequence, and monoclonal antibodies for LAPTM4B are important in studying the effects of LAPTM4B-35 and LAPTM4B-24 in cancer diagnosis and treatment (FIGS. 2, 3, 8, 11, 12, 14, 15). For example, LAPTM4B-EC2$_{232-241}$-pAb, LAPTM4B-N$_{1-99}$-pAb polyclonal antibodies and LAPTM4B-N$_{1-99}$-mAb monoclonal antibody can be used to analyze LAPTM4B protein expression, intracellular localization, separation and purification, and protein-protein interaction. They can also be used to detect the antibody and antigen of LAPTM4B in blood (FIG. 8). Moreover, LAPTM4B-EC2$_{232-241}$-pAb can inhibit cancer cell proliferation (FIG. 12), Tyr$_{285}$ phosphorylation of LAPTM4B protein (FIG. 15-B), and the phosphorylation and activation of signal molecules FAK (FIG. 16-A) and MAPK (FIG. 16-B). Therefore, all the monoclonal and polyclonal antibodies for SEQ ID No: 4 LAPTM4B-35 protein epitope are encompassed in this invention.

SEQ ID No: 8 is the promoter sequence of LAPTM4B gene. To study the regulation of LAPTM4B gene expression, the LAPTM4B gene promoter and the upstream sequence SEQ ID No: 8 are cloned. There are no typical CCAAT (TTGCGCAAT), TATA cassettes in LAPTM4B gene promoter region. But various binding sites of transcription factors exist in the upstream region of LAPTM4B promoter, such as CREBP1/c-Jun, CEBP, PAX2/5/8, GATA, STAT, c-Ets-1, E2F, LYF-1, and c/v-Myb (FIG. 17A). These transcription factors may specifically regulate LAPTM4B expression in cells of various tissues. The abnormal expression and activation of these transcription factors in cancer cells possibly lead to an unbalanced expression of LAPTM4B proteins. Moreover, there are two highly homologous repeating sequences in the upstream domain of LAPTM4B promoter. It is worthwhile to study whether they are responsible to the regulation of LAPTM4B expression. A series of vectors consisting upstream region sequences of LAPTM4B promoter with different lengths—promoter-5' UTR-35 bp encoding region—luciferase reporting gene is constructed, and these vectors are used to transfect into BEL7402 cells and HLE cells from human hepatocellular carcinoma HCC. As shown in FIG. 17, the cells transfected with various vectors all show luciferase activity with various intensities, indicating the transcription activities in these segments. The smallest fragment is a DNA segment (pGL-PF4) at about 38 bp in the upstream region of the transcription starting site. It possesses a basic promoting activity and functions as LAPTM4 core promoter. The activity of pGL-PF4 transfectant in BEL7402 is 20% of the reference promoter SV40, while the activity is low in HLE, only 6% of SV40 activity, about ⅓ of that in BEL7402. These data partially reflect the natural activity of LAPTM4B promoter in these two cell lines. It is consistent with the Northern blot results, where mRNA expression is high in BEL-7402 cell line and low in HLE cell line. Additionally, pGL3-PF4 transfectant reveals dramatically different activities in these two cells. Its activity in BEL-7402 cells is 7 times higher than that in HLE cells. Apparently, different regulative mechanisms of LATPM4B gene transcription exist in BEL7402 and HLE cell lines.

In embodiments of this invention, the genome DNA is genotyped in order to determine the relationship between different LATPM4B genotypes and susceptibility of hepatocellular carcinoma. LATPM4B has two alleles, LATPM4B*1 and LATPM4B*2, i.e., SEQ ID No: 6, is derived by PCR cloning. As shown in FIG. 9, the difference between alleles *1 and *2 is the 19 bp sequence in the first exon 5' UTR. Allele *1 has only one such sequence (nt 124~142dup, while *2 contains two such sequences in a tightly tandem arrangement (124-142dup, taking G at the transcription starting site TSS as +1 numbering standard). The insertion of the 19-bp sequence would eliminate the stop codon in 5'UTR in the corresponding *1 allele by a triplet shift. As a result, the open reading frame may be extended upstream by 53 amino acids at N terminus of the protein. The encoded protein by SEQ ID No: 6 then should contain 370 amino acid residues (SEQ ID No: 7). LATPM4B genotypes detected in human population are *1/*1, *1/*2 and *2/*2, respectively (FIG. 10). Studies show that the risk of developing hepatocellular carcinoma for individuals with LATPM4B genotype *2/*2 is 2.89 times higher than individuals with non-*2/*2 type (Table 2). However, LATPM4B genotype in patients with esophagus carcinoma shows no difference from the normal population (Table 3). This indicates that LATPM4B *2/*2 genotype correlates especially to susceptibility of hepatocellular carcinoma. As a result, LATPM4B allele LATPM4B*2 provided by this invention can be used as a target to screen and diagnose people susceptible to hepatocellular carcinoma or having a high risk to develop hepatocellular carcinoma. Particularly, using LATPM4B *2/*2 genotype as a target to screen highly susceptible or high risk people can be more accurate. *1/*1, *1/*2 and *2/*2 of LATPM4B genotypes, LATPM4B*2 encoded proteins or their antibodies, and/or LATPM4B extender and scavenger from human genome can all be used to screen people who are susceptible to hepatocellular carcinoma or having a high risk to develop hepatocellular carcinoma.

The expression vectors containing sequences described in SEQ ID No: 1, 2, 3, 6, 8, the transfection cell lines containing SEQ ID No: 1, 2, 3, 6, 8 sequences, and the primers amplifying SEQ ID No: 1, 2, 3, 6, 8 are all encompassed by this invention.

BRIEF DESCRIPTION OF THE DRAWINGS

FIG. 1-A is the Northern Blot analysis profiles indicating the transcriptive expression of the gene of this invention in normal human liver, normal fetus liver and hepatocellular carcinoma tissues.

FIG. 1-B is the Northern Blot analysis spectrum indicating the transcriptive expression of the gene of this invention in the human hepatocellular carcinoma cell lines.

FIG. 1-C is a diagram showing the relationship of the expression level of the gene of this invention in human hepatocellular carcinoma tissues and the cancer differentiation status.

FIG. 2-A is a diagram of hybridization in situ of hepatocellular carcinoma tissue. The LATPM4B mRNA in hepatocellular carcinoma nodule shows a strong positive staining.

FIG. 2-B is an immunohistochemical diagram, where LATPM4B protein in hepatocellular carcinoma nodule shows a strong positive staining.

FIG. 2-C is an immunocytochemical diagram, where LATPM4B protein is shown to exist in the transfected cells.

FIGS. 9 A and B shows schematic diagrams of the LAPTM4B promoter and its first exon and the partial sequence (SEQ ID No. 19 and SEQ ID No. 20) of LAPTM4B alleles of this invention.

FIG. 12 is a column diagram showing the inhibitory effect of LAPTM4B-EC2-pAb antibody on proliferation of hepatocellular carcinoma cells.

FIGS. 13-A, 13-B, 13-C, 13-D, and 13-E are the Western Blot analysis diagrams showing respectively that the expressions of cyclin D1, cyclin E, c-Myc, c-Fos, and c-Jun of cDNA-transfected cells of this invention are up-regulated.

FIGS. 14-A, 14-B, and 14-C are the analytical diagrams of the co-immuno precipitation, revealing respectively the interactions of the gene product (LAPTM4B protein) of this invention with α 6 β 1 integrin and with the epidermal growth factor receptor (EGFR).

FIGS. 15-A, 15-B, and 15-C are the analytical diagrams of the immunoprecipitation, showing the Tyr phosphorylation of LAPTM4B protein and the inhibitory effect of LAPTM4B-EC2-pAb on Tyr phosphorylation.

FIGS. 16-A and 16-B are the analytical diagrams of the co-immuno precipitation showing respectively that LAPTM4B is involved in FAK-MAPK signal transduction pathway.

DETAILED DESCRIPTION OF THE INVENTION

Figure 3:
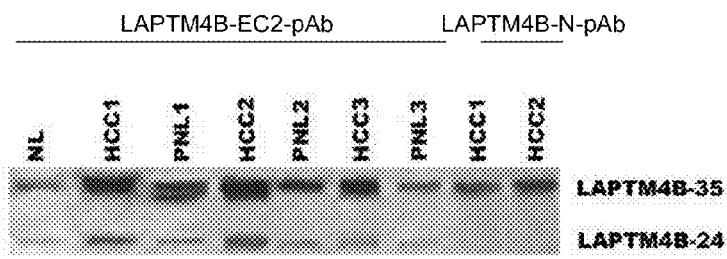
FIG. 3 presents a Western Blot analysis diagram, where the expression spectra of LATPM4B-35 and LATPM4B-24 proteins encoded by the gene of this invention are shown in the tissues of normal liver (NL), hepatocellular carcinoma (HCC), and paired non-cancerous liver (PNL).

Sources of Patients and Normal Control Group:

57 cases of hepatocellular carcinoma patients, 50 males and 7 females, ranged in age from 35-70. Their average age was 54±6.0. The tissues tested came from surgically excised specimens. The blood samples for the control group were collected from 206 similarly aged people with no symptoms and no cancer according to clinic tests and from 209 new born babies' umbilical veins.

109 esophagus cancer patients, 76 males and 33 females, ranged in age from 30-70. Their average age was 55±5.4. The test tissues came from surgically excised specimens. 116 people with no symptoms and no cancer, as determined by clinical examination, were selected as the control group S. Their blood samples were taken for testing. All the samples were extracted to obtain genomic DNA.

Statistical Method

Chi-square ($X^2$) measurement and single factor ANOVA variance were used to treat and analyze the data.

Example 1

Northern Blot Analysis of LAPTM4B Expressions in Four Types of Liver Tissues at Various Proliferation and Differentiation Status Four types of liver tissues at various proliferation and differentiation status were chosen. They were from normal adult livers (NL, with very little proliferation and high differentiation), fetus livers (FL, at vigorous proliferation and low differentiation), hepatocellular carcinoma (HCC, out of controlled proliferation and abnormal differentiation), and paired non-cancerous livers (PNL, generally is of pre-cancerous stage in an active proliferation status). The Northern Blot analysis was used to detect the transcription of gene in these tissues. RNA samples were extracted from 5 normal adult liver tissues freshly obtained from surgical excision: 5 liver tissues from abortive fetus, 55 HCC tissues, and 55 paired non-cancerous liver tissues. After electrophoretic separation, they were transferred to a nylon film and hybridized by Dig labeled probe. The film was washed at 68° C. and the hybridization signals were developed according to the manual. The results are shown in FIG. 1. Band 1 was the sample from fetus livers. Band 2 was from the normal adult liver sample. Bands 3, 5, 7, and 9 were the samples from HCC. Bands 4, 6, 8, 10 were from PNL tissues. The results show that the expression of LAPTM4B in various liver tissues has the following order: HCC tissue>PPNL tissue and fetus liver tissue>normal adult liver tissue.

Example 2

Clonings of LAPTM4B Gene, Allele, and Promoter 2-1 LAPTM4B Gene Cloning

By using fluorescence differential display technique, an unknown gene cDNA segment (LC27) was obtained from differential display spectrum in four types of human liver tissues in different proliferation and differentiation status, such as normal adult livers (NL), fetus livers (FL), cancerous livers (HCC), and paired non-cancerous liver (PNL). The LC27 segment (426 bp) was elongated by splicing homogenous sequences according to the EST to the 5' direction, and followed by RACE (rapid amplification of cDNA ends) and the high temperature RT-PCR techniques. Two full-length cDNA sequences, i.e., SEQ ID No. 2 and 3, were produced, and then confirmed by sequencing and BLAST program analysis.

2-2. LAPTM4B Promoter Cloning

The sequence of upstream region of the first exon of LAPTM4B gene at 5' terminal was obtained by biological informatics, and primers F1 and R1 were designed. Using human genomic DNA from HCC as the template, LAPTM4B promoter and the upstream sequence was obtained by PCR using Platinum Pfx DNA polymerase. After Xho I and hind III enzyme cutting, they were inserted into pGL3-Basicvector to form pGL3-PF1, and its sequence was determined (i.e., the test result see portion a of FIG. 16).

Figure 17:
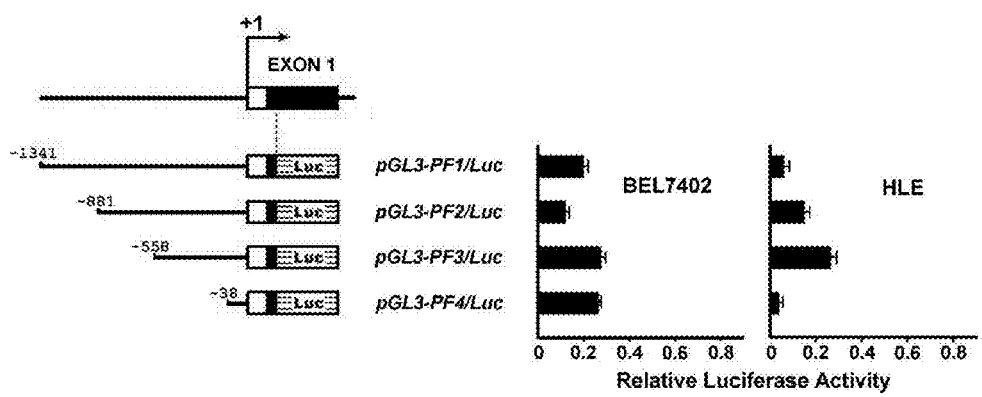
FIG. 17 is a plot showing the transcriptive activity of various fragments of LAPTM4B promoter of this invention (SEQ ID No. 8).

As shown in FIG. 17a, no typical CCAAT (TTGCG-CAAT) and TATA boxes were found in the LAPTM4B promoter sequence. In the upstream region of LAPTM4B promoter, there are many binding sites for a variety of transcription factors, such as CREBP1/c-Jun, CEBP, PAX2/5/8, GATA, STAT, c-Ets-1, E2F, LYF-1, and c/v-Myb. They may function on regulation of LAPTM4B expression. In hepatocellular carcinoma, the abnormal expression and activation of these transcription factors possibly lead to an unbalanced expression of LAPTM4B proteins. Moreover, the LAPTM4B upstream region contains two highly homologous repeating sequences. It is worthwhile to further study on whether they have any effect on LAPTM4B expression regulation.

2-3. Cloning and Sequence Analysis of LAPTM4B Alleles
2-3-1. DNA Separation

Genome DNA was extracted from blood lymphocytes or cancer tissue samples from surgical excision of hepatocellular carcinoma and esophagus carcinoma according to the standard phenol-chloroform method.

2-3-2. Cloning and Sequence Analysis of the Alleles

By using the same procedures for the promoter sequence cloning, two primers,

```
                                        (SEQ ID No. 11)
F1: 5' GCGCTCGAGGCTCCAGGTGGAAGAGTGTGC 3',
``` inducing XhoI enzyme cutting site at 5' terminal sequence as indicated by underlining), and

```
                                        (SEQ ID No. 16)
R1: 5' GCGAAGCTTGGACTTGGCCATGTGACCCG 3',
``` inducing XhoI enzyme cutting site at 5' terminal sequence as indicated by underlining), were designed and synthesized based on LAPTM4B gene sequence SEQ ID No. 3. The promoter sequence and its anterior sequence in the first exon of LAPTM4B were then cloned from human genomic DNA by PCR. The pGL3-PF1 vectors constructed from various human genomic DNA were sequenced to screen the LAPTM4B alleles. The original LAPTM4B sequence was designated as LAPTM4B*1. The other one was designated as LAPTM4B*2, i.e., SEQ ID No. 6 in the sequence listings. FIG. 9(A) shows the schematic diagrams of the LAPTM4B promoter and its first exon. The rectangle frame indicates the first exon, the black color area represents the encoding area, the white color is the non-coded area, and the gray area shows a 19 bp DNA sequence. The horizontal line representing promoter part and F1, F2, R1, and R2 are where the four primers are located. "A" in the start codon ATG is defined as +1 in the sequence. FIG. 9 (B) shows the partial sequences of the LAPTM4B alleles and their sequencing graphic spectra. The underlined part is a 19 bp DNA sequence.

The results reveal that LAPTM4B*1 contains one copied 19 bp DNA sequence and LAPTM4B*2 has two copied 19 bp DNA sequences, which are linked in the non-coded area (nt −33--15) of the first exon of LAPTM4B*1.

The sequence analyses indicate that LAPTM4B*2 and LAPTM4B*1 possess the same promoter. There is no difference in sequences between LAPTM4B alleles *1 and *2 promoters.

2-3-3. LAPTM4B Genotype Classification

```
E2 (5' GCCGACTAGGGGACTGGCGGA 3', SEQ ID No. 9)
and

R2 (5' CGAGAGCTCCGAGCTTCTGCC 3', SEQ ID No. 10)
``` primers were designed and synthesized. A partial sequence of the first exon of LAPTM4B was amplified by PCR using templates of genomic DNA from normal people, hepatocellular carcinoma, and esophagus carcinoma tissues. PCR conditions were as follows: 96° C. pre-denature for 5 min; 94° C. for 30 s, 68° C. for 30 s, 72° C. for 1 min, 35 cycles; 72° C. for 5 min; then the PCR products were conducted to 2% Agarose gel electrophoresis analysis.

Figure 10:
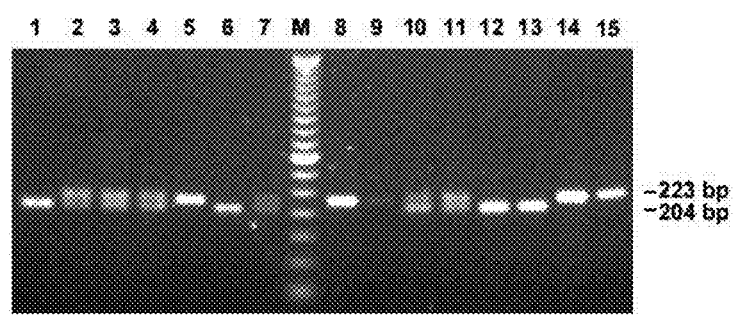
FIG. 10 shows the genotypes distribution of LAPTM4B alleles of this invention in human population.

FIG. 10 shows LAPTM4 gene *1/*1, *1/*2, and *2/*2 three types in human population.

Example 3

Construction of the Reporter Plasmids and Analysis of the Promoter Activity

A series of vectors, that contain the upstream sequences with various length of the LAPTM4B promoter, 5'UTR, the 35 bp encoding sequence in exon and the luciferase reporting gene, were constructed, i.e., the LAPTM4B gene promoter and the upstream sequence was cut by Xho I and I Hind III enzyme and connected to pGL3-Basic vector to form pGL3-PF1, and identified by sequencing. Then pGL3-PF1 was used as a template, primers F2, F3, and F4 vs. R1 were used to amplify by PCR, respectively, to construct vectors, pGL3-PF2, pGL3-PF3, and pGL3-PF4 which contain promoter segments with various lengths and luciferase gene. These constructs were identified by sequencing.

The sequences of these primers are as follows:

```
F1: 5'GCGCTCGAGGCTCCAGGTGGAAGAGTGTGC 3
(nt -1341--1321, SEQ ID No. 17)

F2: 5' GCGCTCGAGTAA AAACGCTGTGCCAGGCGT 3'
(nt -881--861, SEQ ID No. 18)

F3: 5' CCGCTCGAGTACCGGAAGCACAGCGAGGAT 3'
(nt -558--538, SEQ ID No. 13)

F4: 5' GCGCTCGAGAGTAGAAGGGAAGAAAATCGC 3'
(nt -38--18, SEQ ID No. 14)

R1: 5' GCGAAGCTTGGACTTGGCCATGTGACCCG 3'
(nt 172-191, SEQ ID No. 15)
```

These vectors were used to transfect BEL-7402 cells and HLE cells separately and the promoter activities were measured. As shown in FIG. 17b, the vector-transfected cells all have luciferase activities with different intensities. pGL3-PF3 showed similar activity in both BEL-7402 cells and HLE cells, which was about 27% of the SV40 promoter (pGL3-Promoter) activity. When comparing it with pGL3-PF4 activity, however, there was almost no difference in BEL-7402 cells. In HLE cells, pGL3-PF3 activity was 7 times higher than pGL3-PF4. As shown in FIG. 17a, pGL3-PF3 (−41~−558) has many potential binding sites for transcription factors. One or many of them, especially c-Ets-1, may play a regulating role in HLE cells and make the luciferase activities of pGL3-PF3 and pGL3-PF4 tranfectants remarkably different in HLE cells. The pGL3-PF3 activity is higher than that of pGL3-PF1 and pGL3-PF2 in both BEL-7402 and HLE cells, implying that some negatively regulatory factor exists. One or more of these negatively regulatory factors bind with the promoter upstream target sequence (−558 upstream) to induce a downregulated LAPTM4B gene expression. This suppressive effect was stronger in HLE cells than in 7402 cells. This means that HLE cells may contain some factors that strongly suppress the expression of LAPTM4B. The Northern Blot analysis presented in FIG. 1-B also shows a low expression of LAPTM4B in HLE cells, supporting the above hypothesis. The pGL3-PF2 vector contains two DNA repeating fragments (−41~−328, −574~−859), which is one more DNA fragment (−574~−859) than pGL3-PF3. pGL3-PF3 exhibits higher activity than pGL3-PF2 in both cells. This result indicates that the two repeating sequences negatively regulate gene transcription. They have many potential binding sequences for the transcription factors and provide two binding sites for each negatively regulating factor. Since many transcription factors often form dimers, they have to bind with two target sequences to be able to function. In the case of pGL3-PF3, which can only provide one binding site, no function is shown. Since the pGL3-PF3 transfectant has a disinhibitory effect, its activity is higher than other vector transfectants.

Example 4

Western Blot Analysis of LAPTM4B Protein Expression

The tissue sample was placed on ice and cut into small pieces by scissors. 0.1 gram of wet tissue was selected and placed in a manually operated homogenizer. 1 mL lysis buffer was added in each tube and the mixture was thoroughly homogenized. The lysate was transferred to a fresh tube and centrifuged at 4° C., 12 000 g for 10 min to remove the debris. If cells are used, the cells in a culture dish were digested with 0.25% trypsin buffer, followed by two PBS rinses and centrifuged at 500 g for 3 min. The cleared supernatant was collected, and the proteins in the supernatant were separated by SDS-PAGE electrophoresis, and then transferred to the NC membrane. The membrane was blocked at 4° C. overnight with 5% non-fat powdered milk in a TBS buffer containing 0.05% Tween 20. Then it was incubated with the rabbit polyclonal antibody, LAPTM4B-EC2 $_{232-241}$-pAb (1:500 dilution) or mouse Anti-FLAG M2 monoclone antibody (Sigma, 1:750 dilution) at room temperature for 2 hours, and then rinsed with TBS for three times. It was further incubated with a peroxidase-coupled second antibody (IgG), such as goat anti rabbit or goat anti mouse (1:3000 dilution), for 2 hrs, followed by three rinses with a TBS buffer (pH 8.0, containing 0.05% Tween 20). The last wash was with a buffer containing no Tween 20. ECL (Santa Cruz) was used to expose the positive bands (performed as manufacturer's instructions). When two antibodies were sequentially hybridized in one membrane, the ECL exposed membrane was rinsed first with TBS followed by washing with 30 mL TBS (2% SDS and 210 μL β-mercaptoethanol) for 30 min at room temperature. The 30 min TBS rinse removed the previous antibody and its signal in the membrane, which then could be used for the second hybridization. FIG. 3 shows that LAPTM4B-35 was over expressed in HCC tissues and HCC cell lines.

Example 5

Regulatory Effect of the Gene of this Invention on Cell Proliferation and the Malignant Phenotype of Cancer Cells as Demonstrated by a Full-Length cDNA Transfection Using pGEMT-E2E7 plasmid as a template and the PCR method, a full length or partial cDNA, or the reading frame of LAPTM4B gene was amplified by PCR with primers A, or B and E, and the Pfx DNA polymerase. BamHI enzyme cutting site (GGATCC) and ribosome binding site sequences (GCCACC) were introduced in primer A and B at 5' terminal and EcoRI enzyme cutting site (GAATTC) was incorporated in the primer E. The amplified products AE and BE were digested by restriction enzymes BamHI and EcoRI, purified, and ligated into pcDNA 3.0 vector. They were transformed conventionally to DH5 E. coli and the positive clone was selected, and the constructed plasmid was sequenced for identifying. The constructed plasmids were named as pcDNA3/AE and -BE, respectively. pcDNA3/AE contains a full-length ORF, while pcDNA3/BE contains the ORF starting from the second ATG to TAA. Compared with pcDNA3/AE, pcDNA3/BE-encoded protein is missing 91 amino acids at the N terminal.

Figure 4:
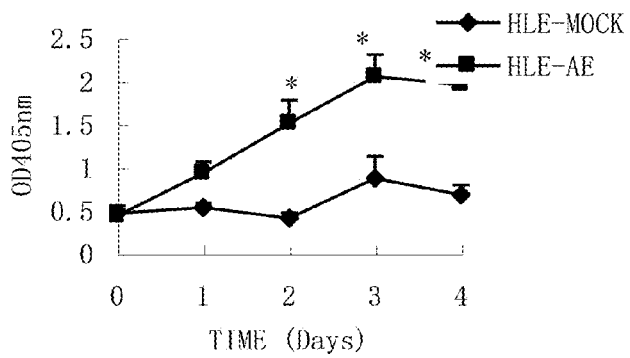
FIG. 4 shows a growth curve of the accelerated proliferation of cDNA-transfected cells of this invention.
Figure 5:
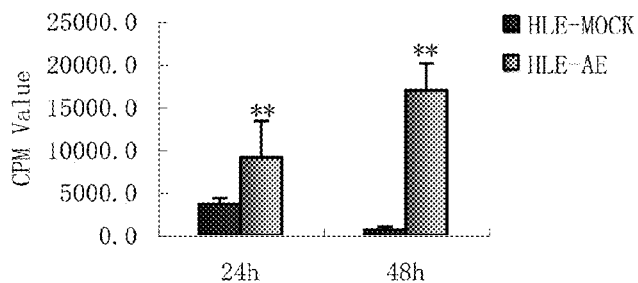
FIG. 5 shows a column diagram, where the DNA synthesis of LAPTM4B cDNA-transfected cells of this invention is increased.
Figure 6:
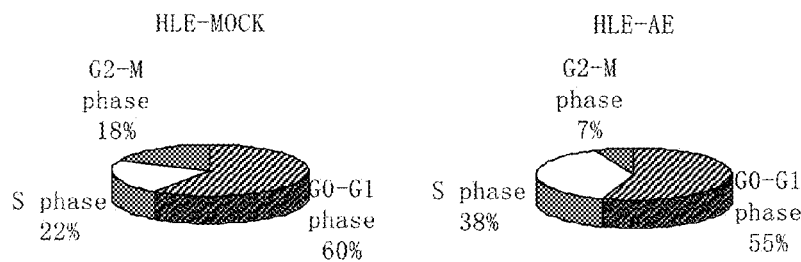
FIG. 6 is a pie diagram showing an increase of cell numbers in S phase in cDNA-transfected cells of this invention (Flow cytometry analysis).

Mouse BHK, NIH3T3 cell lines and human hepatocellular carcinoma HLE cell line, in which the expression of LAPTM4B were all at very low level, were transfected by pcDNA3/AE or -BE, and clones that LAPTM4B expression were stable and high were selected. The total viable cell numbers were determined by the acidic phosphatase method and the cell growth curve was plotted. The cell cycle was analyzed by the flow cytometry. The expression levels of cell cycle-regulating protein, including cyclin D1 and Cyclin E, and proto-oncogene products, including c-Myc, c-Fos, and c-Jun (transcription factors for regulating cell proliferation) were measured by the Western Blot analysis. The results show that the cell proliferation was accelerated after being transfected by LAPTM4B-AE expressive plasmid (FIG. 4, 5, 6). Expressions of cyclin D1, cyclin E, c-Myc, c-Fos, and c-Jun were also greatly increased (FIG. 13-A, B, C, D, E, respectively). But the dependence of growth on serum in LAPTM4B-35-overexpressed cells was greatly reduced (HLE-AE cell proliferation proceeded normally in 1% FCS, but HLE and HLE-MOCK cells stop proliferation at the same condition). In the meantime, the anchorage-dependent cell growth of HLE-AE cells was clearly weakened. Large colonies of HLE-AE cells were formed in the soft agar, which indicates that this gene participated in the regulation of cell proliferation and its over expression (activation) was related to the dysregulation of cell proliferation. Furthermore, the migrating capability of HLE-AE cells was also enhanced (The HLE-AE cells that migrated through the membrane pores were increased from 1216±403.8 for the control to 4082.5±748.8). Its capability to invade Matrigel was also greatly increased (from 25±12.73 cells for the control to 1325±424.26 cells). The results show that LAPTM4B over expression promotes the development of cell malignant phenotype. On the contrary, BHK-BE, NIH3T3-BE, and HLE-BE cells transfected by LAPTM4B-BE expressive plasmid could not form clones. They were all dead within three weeks. These results demonstrate that LAPTM4B-24 plays antagonistic roles to LAPTM4B-35.

Example 6

Tumorigenic Effect of LAPTM4B cDNA-Transfected Cells on Mouse

Figure 7:
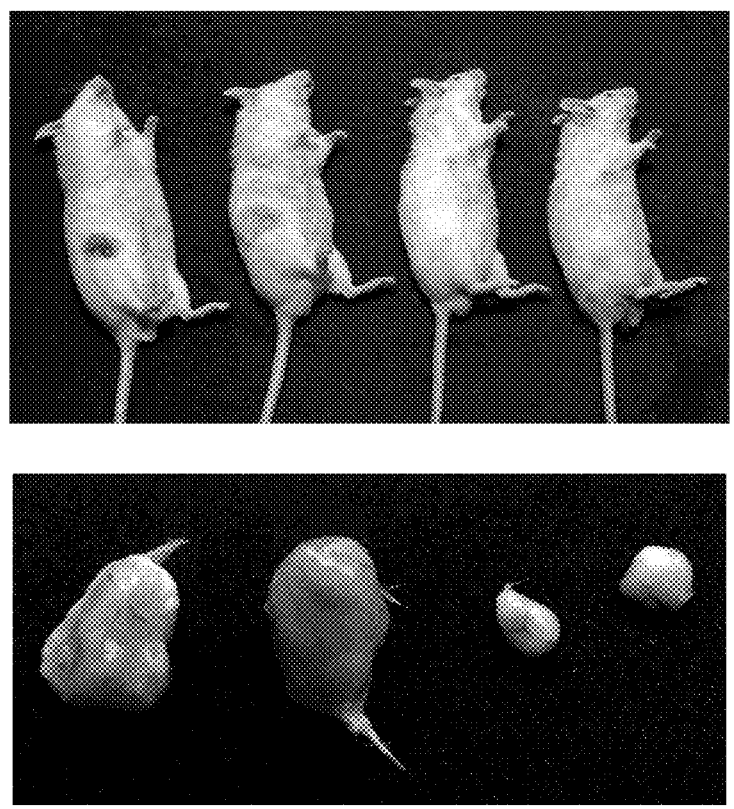
FIG. 7 shows the oncogenic effect of cDNA-transfected cells of this invention on mouse (SEQ ID No. 19).

Six-week old male mice were randomly selected and divided into three groups: In the first control group, the mice were injected with physiological saline. In the second control group, the mice were inoculated with the pcDNA3 MOCK (no-load plasmid) transfected cells by. In the test group, all the mice were inoculated with pcDNA3/AE (a plasmid containing full-length cDNA) transfected NIH3T3 cells. Each mouse was subcutaneously inoculated with $2 \times 10^6$ cells. There were four to six mice in each group. The mice were sacrificed after 21 days inoculation and dissected. As shown in FIG. 7, two mice (half of inoculated mice) in the test group developed a clearly moderate malignant fibrosarcoma (A, B); the other two mice were identified as lymphatic tissue at the inoculated sites (C, D). In contrast, twelve mice in the two control groups showed no sign of tumor formation after being inoculated for 86 days.

The results in Examples 4, 5, and 6 indicate that LAPTM4B may be a novel proto-oncogene.

Example 7

Figure 8:
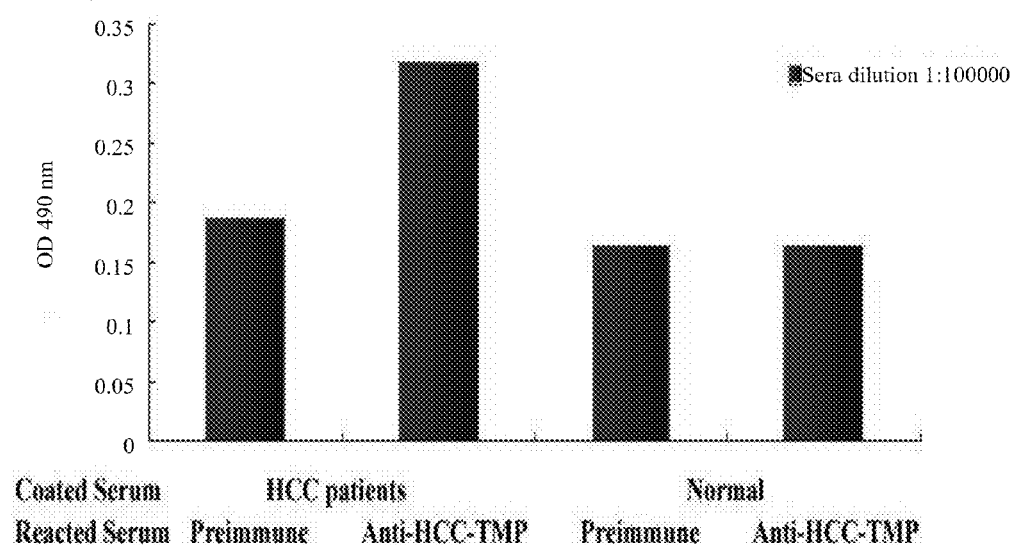
FIG. 8 is a histogram showing the level of the antigen of this invention in the serum of patients with hepatocellular carcinoma.

Primary Analysis of LAPTM4B Antigen in the Serum of Patients with Hepatocellular Carcinoma by the ELISA Method 96 wells culture plates were coated with sera in various dilutions from HCC patients and normal people by known agreement at 4° C. overnight. Each well was washed with 0.5% Tween-20 washing solution, and then 2% BSA was added for blocking at room temperature for 1 hour. Then LAPTM4B-EC2-pAb antibody in various dilutions was added and incubated for 2 hours at room temperature. The goat anti-rabbit antibody labeled by horseradish peroxidase (1:1000 times dilution) was added after PBS washing. After standing at room temperature for 2 hours and one PBS washing, 1 g/mL o-phenyldiamine was added for 10-15 minutes to develop color and $H_2SO_4$ was used to stop the reaction. The microtiter for enzyme analysis was used to measure OD. at 490 nm and the antigen level was estimated. The results are shown in FIG. 8. Clearly, the sera of patients with hepatocellular carcinoma contained higher level of LAPTM4B antigen than that from normal people, indicating that LAPTM4B has a potential to become a new marker for hepatocellular carcinoma diagnosis.

Example 8

Functional Determination of LAPTM4B Protein in Signal Transduction by Co-Immunoprecipitation and Antibody Inhibition Analysis The cell lysate was prepared according to the method in Example 4. The first antibody was added to the supernatant. After 1 hour's shaking at 4° C., 50 µL protein G-Agarose suspension was added and the mixture was shaken at 4° C. for at least three hours or overnight. The immunocomplex precipitate was collected after centrifuging at 12000 g for 20 seconds. The complex was re-suspended by adding 1 mL washing buffer I and shaken at 4° C. for 20 min. The mixture was centrifuged at 12000 g for 20 seconds and the supernatant was removed carefully. This step was repeated once. Then the complex was re-suspended by adding washing buffer II, shaken at 4° C. fro 20 min., and centrifuged at 12000 g for 20 seconds. The supernatant was removed carefully. The last two steps were repeated once. The complex was re-suspended by adding washing buffer III, shaken at 4° C. fro 20 min, and followed by 12 000 g centrifugation for 20 seconds. The supernatant was removed completely. 50 µL 1×SDS loading buffer was added in the precipitate and the mixture was boiling in 100° C. water bath for 5 min to denature and dissociate the immunocomplex in the sample. After 12000 g centrifugation for 20 second, the supernatant was removed and analyzed in SDS-PAGE apparatus.

BEL-7402 cell was preincubated for 0, 10, 20, and 40 min, respectively, on LN-1 substance in serum free medium. Co-immunoprecipitation was performed with LAPTM4B-EC2-pAb from the cell lysate. The co-immunoprecipitates were respectively adsorbed by Protein G-Sephorose, centrifuged, and analyzed by 10% non-reductive SDS-PAGE. Then the phosphorylations of LAPTM4B, FAK and MAPK were analyzed separately by the Western Blot with p-Tyr mAb.

BEL-7402 cells were preinoculated separately with LAPTM4B-EC2-pAb (15 µg/mL) and anti-Glut2 (15 µL/mL) antibodies at 37° C. under 5% $CO_2$ for 2 hrs, and then seeded on LN-1 substance and incubated for indicating time. Under the same conditions, the anti-Glut2 antibody treated cells and no antibody treated cells were used as control. The cell lysate in each group was analyzed by the Western Blot analysis with p-Tyr mAb. The inhibitory effects of various antibodies on phosphorylation of LAPTM4B were analyzed. The results show that LAPTM4B-35 was phosphorylated peakly when human hepatocellular carcinoma BEL-7402 cells were attached on laminin substrate. The phosphorylation of LAPTM4B-35 reached the highest level in 10 min after cell attachment (FIG. 15-A). Meanwhile LAPTM4B-EC2-pAb could inhibit almost completely its phosphorylation (FIG. 15-B), while the anti-Glut2 (an antibody against a non-related plasma membrane protein Glut2) showed no such inhibitory effect (FIG. 15-C). On contrary, LAPTM4B-24 cannot be phosphorylated. The phosphorylation of LAPTM4B-35 $Tyr_{285}$ would form a binding site for signal molecules that contain SH2 domain. In the meantime, LAPTM4B-35 itself presents typical binding sites for signal molecules that contain SH3 domain. Therefore, LAPTM4B-35 functions most likely as a very important docking protein of molecules for signal transduction or a special organizer of membrane microdomain. It could recruit signal molecules related inside or outside cells, so that to play pivotal roles in signal transduction associated with cell proliferation, differentiation and apoptosis. Moreover, the attachment of human hepatocellular carcinoma cells on laminin substrate can also cause Tyr phosphorylation of the cytoplasmic signal molecule FAK (FIG. 16-A), and the LAPTM4B-EC2-pAb and anti-integron α 6 mAb against the epitope of the extracellular region of α6 both can prevent FAK phosphorylation without affecting the expression level of FAK protein by preincubating with BEL 7402 cells. Similarly, the attachment of BEL 7402 cells on laminin substrate can also induce Tyr phosphorylation of the signal molecule MAPK (FIG. 16-B), and its phosphorylation can be inhibited by preincubating cells with LAPTM4B-EC2-pAb without changing the expression level of MAPK protein. These results indicate that the interaction between LAPTM4B-EC2 domain (the second extracellular region) and integrin α6 subunit plays an important role in triggering FAK-MAPK signaling pathway.

The results from Examples 4-8 suggest that LAPTM4B-35 can be potential targets of drugs for regulating cell proliferation, differentiation, and apoptosis.

Example 9

LAPTM4B Genotype Classification

LAPTM4B genotypes in genomic DNA from blood of normal individuals and patients with hepatocellular carcinoma were detected by PCR. Two primers were designed and synthesized according to the flanking sequence of 19 bp DNA sequence in LAPTM4B gene sequence 3:

```
                                      (SEQ ID No. 9)
E2: 5' GCCGACTAGGGGACTGGCGGA 3'

(SEQ ID No. 10)
R2: 5' CGAGAGCTCCGAGCTTCTGCC 3'
```

The partial sequence of the first exon was amplified using genomic DNA as a template. PCR conditions were as follows: 96° C. pre-denature for 5 min, 94° C. for 30 sec, 68° C. for 30 sec, 72° C. for 1 min, 35 cycles, 72° C. extension for 5 min. PCR products were analyzed by 2% agarose gel electrophoresis and the results are shown in FIG. 10. The lanes 1, 6, 12, and 13 represent a 204 bp nucleotide segment in LAPTM4B*1/*1. The lanes 5, 8, 9, 14, and 15 represent a 223 bp nucleotide segment in LAPTM4B*2/*2. The lanes 2, 3, 4, 7, 10, and 11 represent 204 bp and 223 bp nucleotide segments in LAPTM4B*1/*2. Line M is the marker. The results reveals that in the homozygous gene pair of *1/*1 or *2/*2 either the 204 bp or 223 bp DNA segment was amplified, while in *1/*2 hybrid gene pair 204 bp and 223 bp DNA segments were both amplified simultaneously. Therefore, the genotype of LAPTM4B in Chinese population can be classified as LAPTM4B*1/*1, *1/*2, and *2/*2 (FIG. 10).

Example 10

Frequency Distribution of LAPTM4B Genotypes and Alleles in Normal People and Patients with Hepatocellular Carcinoma In one of the embodiments of the present invention, the occurrence frequency of LAPTM4B genotypes in 209 normal Chinese and 57 patients with hepatocellular carcinoma was analyzed and compared in Table 2. The Hardy-Weinberg equation was used to get the expectancy analysis. The frequency of LAPTM4B allele *1 and *2 from patients with hepatocellular carcinoma differs significantly from that of normal people. Their ratios are 0.5175: 0.6746 and 0.4825: 0.3254, respectively. The occurrence frequencies of LAPTM4B allele *1 and *2 in a normal population are 0.6746 and 0.3253, while the occurrence frequency of LAPTM4B allele *1 and *2 in patients with hepatocellular carcinoma are 0.5175 and 0.4825. The occurrence frequency of genotype *1/*1 (p=0.029) and *2/*2 (p=0.003) in the group of hepatocellular carcinoma patient shows a significant statistical difference from its control group. In the hepatocellular carcinoma patient group, only 29.8% is of *1/*1, while in the normal control group, 45.93% is of *1/*1. The occurrence frequency of *2/*2 genotype in the hepatocellular carcinoma patient group is 26.32% as compared to 11.01% in the control group, therefore its occurrence frequency is increased significantly (p<0.01). The analysis shows that the risk suffering from HCC of individuals in *2/*2 genotype of is 2.89 times greater than that in other genotype in developing hepatocellular carcinoma. Thus, the LAPTM4B*2/*2 genotype is correlated with the susceptibility of developing hepatocellular carcinoma.

As shown in Table 3, patients with different LAPTM4B genotypes did not show any differences in hepatocellular carcinoma Grade, stage, or HBV infection. 83.3% of the HCC patients have a positive HBV.

TABLE 2

Distribution of LAPTM4B genotype in hepatocellular carcinoma patients and normal population

| | N (%) | | |
|---|---|---|---|
| | Control B (n = 209) | Hepatocellular carcinoma group (n = 57) | P Value |
| LAPTM4B genotype | | | |
| *1/*1 | 96 (45.93) | 17 (29.82) | 0.029[a] |
| *1/*2 | 90 (43.06) | 25 (43.86) | 0.914 |
| *2/*2 | 23 (11.01) | 15 (26.32) | 0.003[b] |
| Frequency of alleles | | | |
| *1 | 0.6746 | 0.5175 | |
| *2 | 0.3254 | 0.4825 | |

[a]OR: 0.500, 95% CI: 0.267-0.939;
[b]OR: 2.888, 95% CI: 1.390-6.003 (OR risk suffering HCC, and 95% CI is confidence interval)

TABLE 3

Clinical data of the hepatocellular carcinoma patients used in LAPTM4B genotype classification

| | LAPTM4B Genotype | | | |
|---|---|---|---|---|
| | *1/*1 | *1/*2 | *2/*2 | P Value |
| Total number | 17 | 25 | 15 | NS |
| Males | 14 | 24 | 12 | |
| Females | 3 | 1 | 3 | |
| Cancer Grade | | | | |
| G1 | 0 | 2 | 0 | NS |
| G2 | 1 | 4 | 8 | |
| G3 | 7 | 7 | 4 | |
| G4 | 9 | 12 | 3 | |
| Cancer stage | | | | |
| I | 0 | 0 | 0 | NS |
| II | 5 | 8 | 5 | |
| III | 4 | 7 | 3 | |
| IV | 8 | 10 | 7 | |
| HBV Infection | | | | |
| Negative | 1 | 4 | 4 | NS |
| Positive | 13 | 16 | 10 | |
| No diagnosis | 3 | 5 | 1 | |

NS: No significant difference

Example 11

Frequencies of Genotype and Allele in Patients with Esophagus Carcinoma

To study if the LAPTM4B genotype is related to the susceptibility of developing other cancers, the genomic DNA from blood of 116 normal people and 109 patients with esophagus carcinoma from the same location were analyzed. As shown in Table 4, LAPTM4B genotype of patients with esophagus carcinoma is no significant different from control group of the normal population. LAPTM4B alleles are not related with the susceptibility of developing esophagus cancer.

TABLE 4

Distributions of LAPTM4B genotypes of patients with esophagus carcinoma and normal population

| | N (%) | | | |
|---|---|---|---|---|
| | Control group B (n = 209) | Control group S (n = 116) | Esophagus carcinoma (n = 109) | P Value |
| | LAPTM4B genotype | | | |
| *1/*1 | 96 (45.93) | 52 (44.83) | 49 (44.95) | >0.05 |
| *1/*2 | 90 (43.06) | 49 (42.24) | 48 (44.04) | >0.05 |
| *2/*2 | 23 (11.01) | 15 (12.93) | 12 (11.01) | >0.05 |
| | Allele frequency | | | |
| *1 | 0.6746 | 0.6595 | 0.6697 | |
| *2 | 0.3254 | 0.3405 | 0.3303 | |

Example 12

LAPTM4B-35 Expression in Some Epithelium Sourced Cancers

Figure 11:
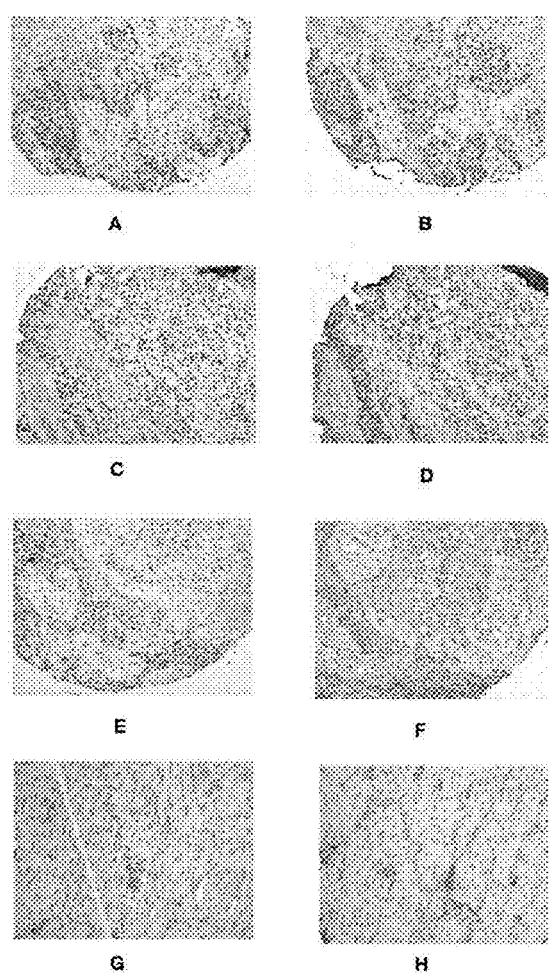
FIG. 11 is an immunohistochemical diagram of various cancer tissues derived from epithelium.

The relationship between the LAPTM4B-35 protein expression and other cancers was studied by an immunohistochemical method. The fixed specimens from esophagus cancer, breast cancer, lung cancer, stomach cancer, colon cancer, and rectal cancer positive tissues and the negative control noncancerous tissues were obtained from surgical excision and treated according to the following steps:
1. Specimen dewaxing by xylene
2. Katocromy with different concentrations of ethanol, 100%-95%-90%-80%-70%. $H_2O_2$ was used to remove endogenous peroxidase
3. Antigen repairing by sodium citrate
4. PBS rinse twice
5. Normal goat serum blocking
6. Keep LAPTM4B-$N_{1-99}$pAb at 37° C. for 1 hour
7. PBS rinse three times
8. Keep HRP labeled goat anti-rabbit antibody at 37° C. for 1 hour
9. PBS rinse three times
10. Develop color by DAB
11. Nuclear retaining with hematoxylin
12. Ascending dehydration by ethanol at different concentrations (70%-80%-90%-95%-100%
13. Mounting As shown in FIG. 11, the 11-A indicates a normal esophagus tissue (Negative), B is an esophagus cancer tissue (Negative), C is a normal breast tissue (Negative), D is the breast cancer tissue (Positive), E is a normal lung tissue (Negative), F is a lung cancer tissue (Positive), G is a normal stomach tissue (Negative), and H is a stomach cancer tissue (Positive). As can be seen from the figures, LAPTM4B was clearly expressed in lung cancer, stomach cancer, and breast cancer tissues, while it was not expressed clearly in esophagus cancer and large intestine cancer.

INDUSTRIAL APPLICATIONS

The proteins encoded by LAPTM4B gene in this invention could be possibly used as new markers in early diagnosis of some cancers. By using the widely applied ELISA method in clinical tests, and the prepared related testing reagent kits, the efficiency and the accuracy of the early diagnosis of cancers, especially the primary hepatocellular carcinoma, can be improved.

LAPTM4B gene can be used as target gene in the cancer treatment. Suppressing LAPTM4B-35 expression and promoting LAPTM4B-24 expression could inhibit the growth of hepatocellular carcinoma cells, reverse malignancy phenotype or delay its development. For example, the expression products of LAPTM4B gene, LAPTM4B-35 could be inhibited by the newly developed siRNA interference technology. Furthermore, LAPTM4B-BE-cDNA could be recombinated in the engineered virus expression vector and be used in antitumor gene therapy through an up-regulation of LAPTM4B-24 expression. LAPTM4B-35 protein could also be used as a new target for pharmaceutical treatment. Since LAPTM4B-35 protein can function as an assembling platform for complex of cell signal transduction molecules, and it contains a number of binding sites for signal molecules, there is a great potential to develop various new medicines with LAPTM4B protein as targets. Moreover, this invention has initially demonstrated that LAPTM4B-EC2-pAb antibody can inhibit tumor cell proliferation and block its signal transduction. Based on the discovery in this invention, further studies can be pursued on the possibility of using antibody to inhibit hepatocellular carcinoma and some other cancer development. After a better understanding on the effect, a humanized soluble single chain antibody could be developed for clinical treatment on HCC patients. Peptide vaccines could also be developed. If the vaccines can be successfully made, it will not only help cure hepatocellular carcinoma and some other cancer, but also prevent cancerogenesis in the high risk population. In summary, many new anticancer approaches can be developed based on the embodiments of this invention. As important supplements for treatments of hepatocellular carcinoma and other cancers, this invention will help increase the cure rates of hepatocellular carcinoma and other cancers. This project would generate a significantly great impact on human society.

In specific embodiments, LAPTM4B genotype of genomice DNA is genotyped. The relationship of various genotypes with the susceptibility to hepatocellular carcinoma as well as with other cancers s is investigated. It is discovered that one of the genotypes, LAPTM4B*2/*2, is correlated closely to hepatocellular carcinoma susceptibility. As a result, it provides a new and accurate criterion for screening people who are susceptible to primary hepatocellular carcinoma in the high risk population. It is of important significance to the assessment and prevention of high risk population from developing hepatocellular carcinoma.

The invention claimed is:

1. An in vitro method of detecting LAPTM4B-35 protein in a human tissue, blood or serum sample, comprising
   (a) obtaining a human tissue, blood, or serum sample;
   (b) detecting the level of LAPTM4B-35 protein in said sample, wherein the amino acid sequence of LAPTM4B-35 protein comprises the amino acid sequence of SEQ ID NO: 4.

2. The method according to claim 1, further comprising detecting the level of LAPTM4B-24 protein in said sample, wherein the amino acid sequence of LAPTM4B-24 protein consists of the amino acid sequence of SEQ ID NO: 5.

3. The method according to claim 2, further comprising the step of determining the ratio of the level of LAPTM4B-35 protein to the level of LAPTM4B-24.

4. The method according to claim 1, wherein the sample is a tissue selected from the group consisting of liver, stomach, breast, lung and prostate.

5. The method according to claim 1, wherein the sample is from a patient at risk of cancer.

* * * * *

SEQUENCE LISTING

<160> NUMBER OF SEQ ID NOS: 20

<210> SEQ ID NO 1
<211> LENGTH: 954
<212> TYPE: DNA
<213> ORGANISM: Homo sapiens -continued

```
<400> SEQUENCE: 1
atgacgtcac ggactcgggt cacatggccg agtccgcccc gcccctccc cgtccccgcc      60 gctgcagccg tcgccttcgg agcgaagggt accgacccgg cagaagctcg gagctctcgg     120
ggtatcgagg aggcaggccc gcgggcgcac gggcgagcgg gccgggagcc ggagcggcgg     180
aggagccggc agcagcggcg cggcgggctc caggcgaggc ggtcgacgct cctgaaaact     240
tgcgcgcgcg ctcgcgccac tgcgcccgga gcgatgaaga tggtcgcgcc ctggacgcgg     300
ttctactcca acagctgctg cttgtgctgc catgtccgca ccggcaccat cctgctcggc     360
gtctggtatc tgatcatcaa tgctgtggta ctgttgattt tattgagtgc cctggctgat     420
ccggatcagt ataactttc aagttctgaa ctgggaggtg actttgagtt catggatgat     480
gccaacatgt gcattgccat tgcgatttct cttctcatga tcctgatatg tgctatggct     540
acttacggag cgtacaagca acgcgcagcc tggatcatcc cattcttctg ttaccagatc     600
tttgactttg ccctgaacat gttggttgca atcactgtgc ttatttatcc aaactccatt     660
caggaataca tacggcaact gcctcctaat tttccctaca gagatgatgt catgtcagtg     720
aatcctacct gtttggtcct tattattctt ctgtttatta gcattatctt gacttttaag     780
ggttacttga ttagctgtgt ttggaactgc taccgataca tcaatggtag gaactcctct     840
gatgtcctgg tttatgttac cagcaatgac actacggtgc tgctaccccc gtatgatgat     900
gccactgtga atggtgctgc caaggagcca ccgccacctt acgtgtctgc ctaa          954

<210> SEQ ID NO 2
<211> LENGTH: 1440
<212> TYPE: DNA
<213> ORGANISM: Homo sapiens

<400> SEQUENCE: 2
gccgactagg ggactggcgg agggtgcacg ctgatggatt tactcaccgg gtgcttggag      60
ctccagcagc tggctggagc ccgcgatgac gtcacggact cggtcacat ggccgagtcc     120 gccccgcccc ctccccgtcc ccgccgctgc agccgtcgcc ttcggagcga agggtaccga     180
cccggcagaa gctcggagct ctcggggtat cgaggaggca ggcccgcggg cgcacgggcg     240
agcgggccgg gagccggagc ggcggaggag ccggcagcag cggcgcggcg ggctccaggc     300
gaggcggtcg acgctcctga aaacttgcgc gcgcgctcgc gccactgcgc ccggagcgat     360
gaagatggtc gcgccctgga cgcggttcta ctccaacagc tgctgcttgt gctgccatgt     420
ccgcaccggc accatcctgc tcggcgtctg gtatctgatc atcaatgctg tggtactgtt     480
gattttattg agtgccctgg ctgatccgga tcagtataac ttttcaagtt ctgaactggg     540
aggtgacttt gagttcatgg atgatgccaa catgtgcatt gccattgcga tttctcttct     600
catgatcctg atatgtgcta tggctactta cggagcgtac aagcaacgcg cagcctggat     660
catcccattc ttctgttacc agatctttga ctttgccctg aacatgttgg ttgcaatcac     720
tgtgcttatt tatccaaact ccattcagga atacatacgg caactgcctc ctaattttcc     780
ctacagagat gatgtcatgt cagtgaatcc tacctgtttg gtccttatta ttcttctgtt     840
tattagcatt atcttgactt ttaagggtta cttgattagc tgtgtttgga actgctaccg     900
atacatcaat ggtaggaact cctctgatgt cctggtttat gttaccagca atgacactac     960
ggtgctgcta ccccgtatg atgatgccac tgtgaatggt gctgccaagg agccaccgcc    1020
accttacgtg tctgcctaag ccttcaagtg ggcggagctg agggcagcag cttgactttg    1080
cagacatctg agcaatagtt ctgttatttc acttttgcca tgagcctctc tgagcttgtt    1140
```

```
tgttgctgaa atgctacttt ttaaaattta gatgttagat tgaaaactgt agttttcaac      1200
atatgctttg ctggaacact gtgatagatt aactgtagaa ttcttcctgt acgattgggg      1260
atataatggg cttcactaac cttccctagg cattgaaact tcccccaaat ctgatggacc      1320
tagaagtctg cttttgtacc tgctgggccc caaagttggg catttttctc tctgttccct      1380
ctcttttgaa aatgtaaaat aaaaccaaaa atagaccaaa aaaaaaaaaa aaaaaaaaa       1440

<210> SEQ ID NO 3
<211> LENGTH: 2169
<212> TYPE: DNA
<213> ORGANISM: Homo sapiens

<400> SEQUENCE: 3
gccgactagg ggactggcgg agggtgcacg ctgatggatt tactcaccgg gtgcttggag        60
ctccagcagc tggctggagc ccgcgatgac gtcacggact cgggtcacat ggccgagtcc       120
gccccgcccc ctccccgtcc ccgcgctgc agccgtcgcc ttcggagcga agggtaccga       180
cccggcagaa gctcggagct ctcggggtat cgaggaggca ggcccgcggg cgcacgggcg       240
agcgggccgg gagccggagc ggcggaggag ccggcagcag cggcgcggcg ggctccaggc       300
gaggcggtcg acgctcctga aaacttgcgc gcgcgctcgc gccactgcgc ccggagcgat       360
gaagatggtc gcgccctgga cgcggttcta ctccaacagc tgctgcttgt gctgccatgt       420
ccgcaccggc accatcctgc tcggcgtctg gtatctgatc atcaatgctg tggtactgtt       480
gattttattg agtgccctgg ctgatccgga tcagtataac ttttcaagtt ctgaactggg       540
aggtgacttt gagttcatgg atgatgccaa catgtgcatt gccattgcga tttctcttct       600
catgatcctg atatgtgcta tggctactta cggagcgtac aagcaacgcg cagcctggat       660
catcccattc ttctgttacc agatctttga ctttgccctg aacatgttgg ttgcaatcac       720
tgtgcttatt tatccaaact ccattcagga atacatacgg caactgcctc ctaattttcc       780
ctacagagat gatgtcatgt cagtgaatcc tacctgtttg gtccttatta ttcttctgtt       840
tattagcatt atcttgactt ttaagggtta cttgattagc tgtgtttgga actgctaccg       900
atacatcaat ggtaggaact cctctgatgt cctggtttat gttaccagca atgcactac       960 ggtgctgcta cccccgtatg atgatgccac tgtgaatggt gctgccaagg agccaccgcc      1020
accttacgtg tctgcctaag ccttcaagtg ggcggagctg agggcagcag cttgactttg      1080
cagacatctg agcaatagtt ctgttatttc acttttgcca tgagcctctc tgagcttgtt      1140
tgttgctgaa atgctacttt ttaaaattta gatgttagat tgaaaactgt agttttcaac      1200
atatgctttg ctggaacact gtgatagatt aactgtagaa ttcttcctgt acgattgggg      1260
atataatggg cttcactaac cttccctagg cattgaaact tcccccaaat ctgatggacc      1320
tagaagtctg cttttgtacc tgctgggccc caaagttggg catttttctc tctgttccct      1380
ctcttttgaa aatgtaaaat aaaaccaaaa atagacaact ttttcttcag ccattccagc      1440
atagagaaca aaaccttatg gaaacaggaa tgtcaattgt gtaatcattg ttctaattag      1500
gtaaatagaa gtccttatgt atgtgttaca agaatttccc ccacaacatc ctttatgact      1560
gaagttcaat gacagtttgt gtttggtggt aaaggatttt ctccatggcc tgaattaaga      1620
ccattagaaa gcaccaggcc gtgggagcag tgaccatctg ctgactgttc ttgtggatct      1680
tgtgtccagg gacatggggt gacatgcctc gtatgtgtta gagggtggaa tggatgtgtt      1740
tggcgctgca tgggatctgg tgcccctctt ctcctggatt cacatcccca cccagggccc      1800
gcttttacta agtgttctgc cctagattgg ttcaaggagg tcatccaact gactttatcg      1860
```

```
agtggaattg ggatatattt gatatacttc tgcctaacaa catggaaaag ggttttcttt      1920
tccctgcaag ctacatccta ctgctttgaa cttccaagta tgtctagtca ccttttaaaa      1980
tgtaaacatt ttcagaaaaa tgaggattgc cttccttgta tgcgcttttt accttgacta      2040
cctgaattgc aagggatttt tatatattca tatgttacaa agtcagcaac tctcctgttg      2100
gttcattatt gaatgtgctg taaattaagt tgtttgcaat taaaacaagg tttgcccaca      2160
aaaaaaaaa                                                              2169
```

<210> SEQ ID NO 4
<211> LENGTH: 317
<212> TYPE: PRT
<213> ORGANISM: Homo sapiens

<400> SEQUENCE: 4

```
Met Thr Ser Arg Thr Arg Val Thr Trp Pro Ser Pro Arg Pro Leu
1               5                   10                  15

Pro Val Pro Ala Ala Ala Val Ala Phe Gly Ala Lys Gly Thr Asp
                20                  25                  30

Pro Ala Glu Ala Arg Ser Ser Arg Gly Ile Glu Glu Ala Gly Pro Arg
                35                  40                  45

Ala His Gly Arg Ala Gly Arg Glu Pro Glu Arg Arg Ser Arg Gln
        50                  55                  60

Gln Arg Arg Gly Gly Leu Gln Ala Arg Ser Thr Leu Leu Lys Thr
65                  70                  75                  80

Cys Ala Arg Ala Arg Ala Thr Ala Pro Gly Ala Met Lys Met Val Ala
                85                  90                  95

Pro Trp Thr Arg Phe Tyr Ser Asn Ser Cys Cys Leu Cys Cys His Val
                100                 105                 110

Arg Thr Gly Thr Ile Leu Leu Gly Val Trp Tyr Leu Ile Ile Asn Ala
                115                 120                 125

Val Val Leu Leu Ile Leu Leu Ser Ala Leu Ala Asp Pro Asp Gln Tyr
        130                 135                 140

Asn Phe Ser Ser Ser Glu Leu Gly Gly Asp Phe Glu Phe Met Asp Asp
145                 150                 155                 160

Ala Asn Met Cys Ile Ala Ile Ala Ile Ser Leu Leu Met Ile Leu Ile
                165                 170                 175

Cys Ala Met Ala Thr Tyr Gly Ala Tyr Lys Gln Arg Ala Ala Trp Ile
                180                 185                 190

Ile Pro Phe Phe Cys Tyr Gln Ile Phe Asp Phe Ala Leu Asn Met Leu
        195                 200                 205

Val Ala Ile Thr Val Leu Ile Tyr Pro Asn Ser Ile Gln Glu Tyr Ile
        210                 215                 220

Arg Gln Leu Pro Pro Asn Phe Pro Tyr Arg Asp Asp Val Met Ser Val
225                 230                 235                 240

Asn Pro Thr Cys Leu Val Leu Ile Ile Leu Leu Phe Ile Ser Ile Ile
                245                 250                 255

Leu Thr Phe Lys Gly Tyr Leu Ile Ser Cys Val Trp Asn Cys Tyr Arg
                260                 265                 270

Tyr Ile Asn Gly Arg Asn Ser Ser Asp Val Leu Val Tyr Val Thr Ser
        275                 280                 285

Asn Asp Thr Thr Val Leu Leu Pro Pro Tyr Asp Ala Thr Val Asn
        290                 295                 300

Gly Ala Ala Lys Glu Pro Pro Pro Tyr Val Ser Ala
305                 310                 315
```

<210> SEQ ID NO 5
<211> LENGTH: 226
<212> TYPE: PRT
<213> ORGANISM: Homo sapiens

<400> SEQUENCE: 5

Met Lys Met Val Ala Pro Trp Thr Arg Phe Tyr Ser Asn Ser Cys Cys
1               5                   10                  15

Leu Cys Cys His Val Arg Thr Gly Thr Ile Leu Leu Gly Val Trp Tyr
            20                  25                  30

Leu Ile Ile Asn Ala Val Val Leu Leu Ile Leu Leu Ser Ala Leu Ala
        35                  40                  45

Asp Pro Asp Gln Tyr Asn Phe Ser Ser Ser Glu Leu Gly Gly Asp Phe
    50                  55                  60

Glu Phe Met Asp Asp Ala Asn Met Cys Ile Ala Ile Ala Ile Ser Leu
65                  70                  75                  80

Leu Met Ile Leu Ile Cys Ala Met Ala Thr Tyr Gly Ala Tyr Lys Gln
                85                  90                  95

Arg Ala Ala Trp Ile Ile Pro Phe Phe Cys Tyr Gln Ile Phe Asp Phe
            100                 105                 110

Ala Leu Asn Met Leu Val Ala Ile Thr Val Leu Ile Tyr Pro Asn Ser
        115                 120                 125

Ile Gln Glu Tyr Ile Arg Gln Leu Pro Pro Asn Phe Pro Tyr Arg Asp
    130                 135                 140

Asp Val Met Ser Val Asn Pro Thr Cys Leu Val Leu Ile Ile Leu Leu
145                 150                 155                 160

Phe Ile Ser Ile Ile Leu Thr Phe Lys Gly Tyr Leu Ile Ser Cys Val
                165                 170                 175

Trp Asn Cys Tyr Arg Tyr Ile Asn Gly Arg Asn Ser Ser Asp Val Leu
            180                 185                 190

Val Tyr Val Thr Ser Asn Asp Thr Thr Val Leu Leu Pro Pro Tyr Asp
        195                 200                 205

Asp Ala Thr Val Asn Gly Ala Ala Lys Glu Pro Pro Pro Tyr Val
    210                 215                 220

Ser Ala
225

<210> SEQ ID NO 6
<211> LENGTH: 2264
<212> TYPE: DNA
<213> ORGANISM: Homo sapiens

<400> SEQUENCE: 6
gaatctcgac ccttgaatgg agttacacga acggccagat gaaagaagga aggcccggac      60
ctccactcag ggccgactag gggactggcg gagggtgcac gctgatggat ttactcaccg     120
ggtgcttgga gctccagcag ctgcttggag ctccagcagc tggctggagc ccgcgatgac     180
gtcacggact cgggtcacat ggccgagtcc gccccgcccc ctccccgtcc ccgccgctgc     240
agccgtcgcc ttcggagcga agggtaccga cccggcagaa gctcggagct tcggggtat      300 cgaggaggca ggcccgcggg cgcacggcgg agcgggccgg gagccggagc ggcggaggag     360
ccggcagcag cggcgcggcg ggctccaggc gaggcggtcg acgctcctga aaacttgcgc     420
gcgcgctcgc gccactgcgc ccggagcgat gaagatggtc gcgccctgga cgcggttcta     480
ctccaacagc tgctgcttgt gctgccatgt ccgcaccggc accatcctgc tcggcgtctg     540
gtatctgatc atcaatgctg tggtactgtt gattttattg agtgccctgg ctgatccgga     600

| | |
|---|---|
| tcagtataac ttttcaagtt ctgaactggg aggtgacttt gagttcatgg atgatgccaa | 660 |
| catgtgcatt gccattgcga tttctcttct catgatcctg atatgtgcta tggctactta | 720 |
| cggagcgtac aagcaacgcg cagcctggat catcccattc ttctgttacc agatctttga | 780 |
| ctttgccctg aacatgttgg ttgcaatcac tgtgcttatt tatccaaaact ccattcagga | 840 |
| atacatacgg caactgcctc ctaattttcc ctacagagat gatgtcatgt cagtgaatcc | 900 |
| tacctgtttg gtccttatta ttcttctgtt tattagcatt atcttgactt ttaagggtta | 960 |
| cttgattagc tgtgtttgga actgctaccg atacatcaat ggtaggaact cctctgatgt | 1020 |
| cctggtttat gttaccagca atgacactac ggtgctgcta ccccgtatg atgatgccac | 1080 |
| tgtgaatggt gctgccaagg agccaccgcc accttacgtg tctgcctaag ccttcaagtg | 1140 |
| ggcggagctg agggcagcag cttgactttg cagacatctg agcaatagtt ctgttatttc | 1200 |
| acttttgcca tgagcctctc tgagcttgtt tgttgctgaa atgctacttt ttaaaattta | 1260 |
| gatgttagat tgaaaactgt agttttcaac atatgctttg ctggaacact gtgatagatt | 1320 |
| aactgtagaa ttcttcctgt acgattgggg atataatggg cttcactaac cttccctagg | 1380 |
| cattgaaact tcccccaaat ctgatggacc tagaagtctg cttttgtacc tgctgggccc | 1440 |
| caaagttggg cattttctc tctgttccct ctcttttgaa aatgtaaaat aaaaccaaaa | 1500 |
| atagacaact ttttcttcag ccattccagc atagagaaca aaaccttatg gaaacaggaa | 1560 |
| tgtcaattgt gtaatcattg ttctaattag gtaaatagaa gtcctttatgt atgtgttaca | 1620 |
| agaatttccc ccacaacatc ctttatgact gaagttcaat gacagtttgt gtttggtggt | 1680 |
| aaaggatttt ctccatggcc tgaattaaga ccattagaaa gcaccaggcc gtgggagcag | 1740 |
| tgaccatctg ctgactgttc ttgtggatct tgtgtccagg acatggggt gacatgcctc | 1800 |
| gtatgtgtta gagggtggaa tggatgtgtt tggcgctgca tgggatctgg tgcccctctt | 1860 |
| ctcctggatt cacatcccca cccagggccc gcttttacta agtgttctgc cctagattgg | 1920 |
| ttcaaggagg tcatccaact gactttatcg agtggaattg ggatatattt gatatacttc | 1980 |
| tgcctaacaa catggaaaag ggttttcttt tccctgcaag ctacatccta ctgctttgaa | 2040 |
| cttccaagta tgtctagtca ccttttaaaa tgtaaacatt ttcagaaaaa tgaggattgc | 2100 |
| cttccttgta tgcgcttttt accttgacta cctgaattgc aagggatttt tatatattca | 2160 |
| tatgttacaa agtcagcaac tctcctgttg gttcattatt gaatgtgctg taaattaagt | 2220 |
| tgtttgcaat taaaacaagg tttgcccaca aaaaaaaaaa aaaa | 2264 |

<210> SEQ ID NO 7
<211> LENGTH: 370
<212> TYPE: PRT
<213> ORGANISM: Homo sapiens

<400> SEQUENCE: 7

Met Glu Leu His Glu Arg Pro Asp Glu Arg Arg Lys Ala Arg Thr Ser
1               5                   10                  15

Thr Gln Gly Arg Leu Gly Asp Trp Arg Arg Val His Ala Asp Gly Phe
            20                  25                  30

Thr His Arg Val Leu Gly Ala Pro Ala Ala Ala Trp Ser Ser Ser Ser
        35                  40                  45

Trp Leu Glu Pro Ala Met Thr Ser Arg Thr Arg Val Thr Trp Pro Ser
    50                  55                  60

Pro Pro Arg Pro Leu Pro Val Pro Ala Ala Ala Ala Val Ala Phe Gly
65                  70                  75                  80

```
Ala Lys Gly Thr Asp Pro Ala Glu Ala Arg Ser Ser Arg Gly Ile Glu
             85                  90                  95

Glu Ala Gly Pro Arg Ala His Gly Arg Ala Gly Arg Glu Pro Glu Arg
            100                 105                 110

Arg Arg Ser Arg Gln Gln Arg Gly Gly Leu Gln Ala Arg Arg Ser
            115                 120                 125

Thr Leu Leu Lys Thr Cys Ala Arg Ala Arg Thr Ala Pro Gly Ala
130                 135                 140

Met Lys Met Val Ala Pro Trp Thr Arg Phe Tyr Ser Asn Ser Cys Cys
145                 150                 155                 160

Leu Cys Cys His Val Arg Thr Gly Thr Ile Leu Leu Gly Val Trp Tyr
                165                 170                 175

Leu Ile Ile Asn Ala Val Val Leu Leu Ile Leu Leu Ser Ala Leu Ala
                180                 185                 190

Asp Pro Asp Gln Tyr Asn Phe Ser Ser Ser Glu Leu Gly Gly Asp Phe
            195                 200                 205

Glu Phe Met Asp Asp Ala Asn Met Cys Ile Ala Ile Ala Ile Ser Leu
            210                 215                 220

Leu Met Ile Leu Ile Cys Ala Met Ala Thr Tyr Gly Ala Tyr Lys Gln
225                 230                 235                 240

Arg Ala Ala Trp Ile Ile Pro Phe Phe Cys Tyr Gln Ile Phe Asp Phe
                245                 250                 255

Ala Leu Asn Met Leu Val Ala Ile Thr Val Leu Ile Tyr Pro Asn Ser
            260                 265                 270

Ile Gln Glu Tyr Ile Arg Gln Leu Pro Pro Asn Phe Pro Tyr Arg Asp
            275                 280                 285

Asp Val Met Ser Val Asn Pro Thr Cys Leu Val Leu Ile Ile Leu Leu
            290                 295                 300

Phe Ile Ser Ile Ile Leu Thr Phe Lys Gly Tyr Leu Ile Ser Cys Val
305                 310                 315                 320

Trp Asn Cys Tyr Arg Tyr Ile Asn Gly Arg Asn Ser Ser Asp Val Leu
                325                 330                 335

Val Tyr Val Thr Ser Asn Asp Thr Thr Val Leu Leu Pro Pro Tyr Asp
            340                 345                 350

Asp Ala Thr Val Asn Gly Ala Ala Lys Glu Pro Pro Pro Pro Tyr Val
            355                 360                 365

Ser Ala
    370

<210> SEQ ID NO 8
<211> LENGTH: 1341
<212> TYPE: DNA
<213> ORGANISM: Homo sapiens

<400> SEQUENCE: 8
gctccaggtg aagagtgtg cagctgcaag atttaataga gtgaaaacag ctcccataca      60
gtgggcgggg acccaaaggg ggttgcccac tcccggctgg aatgcctggg gtttatatcc    120
caatcattgt ccctccccct gtgctctcag atgatagatg atttgactat ttctttacct    180
cttgctttta gcttaattgg tgtttagtg agccctttt actacctgat tggtcaggtg      240
tgagctgagt tacaagcccc atgtttaagg gtgggtgcgg tccccttccc caggtaggtt    300
taggaattct tagtcgcccc aggaaatccg ctactcttgt ctctcactgg gattacaggc    360
gtgagccacc gcgcccagcc aatttttggta tttttttgtag agccagggtt tcgccatgtt    420
```

```
gcccaggctg ggactgaatc tttagagctg cactcatgat taaaaacgct gtgccaggcg      480
ttgtggctca cgcctgtaat cccagcactt tgggaggctg aggcgggcgg atcacgaggt      540
cagaagatcg agaccatcct ggctaacacg gtgaaacccc gtctctactg aaaatacaac      600
aaattagcca ggcgtggtgg cgggcgcctg tagtcccagc tactagggag gctgaggcag      660
gagaatggcg tgaacccggg aggtggagct tgcagtgagc cgagatcgca ccactgcact      720
ccagcctggg tgacagagca agactctgtc tcaaaaaaaa aaaaaaaaaa aaaaaaaaaa      780
agctaccgga agcacagcga ggatgtcctt gacacacatc ctattttctg ggaaaagatt      840
actaccacag taattgagct gtgaagcgga gacaaattgc tctcggtggt ggttcaaagt      900
actgcaattg actggaatag caccgcgcag ttttccttcc tctcgtgcaa gataagagtg      960
ataggagctg tatcgattac ctgcaagata gaagtagaag cgggccgggt gcggtggctc     1020
acgcctgtaa tcccagcact ttgggaggct gaggcgggtg gatcattcga cgtcaggagt     1080
tccagaccag cctgaccaac atggtgaaac cccgtctcta ctaaaaatac aacaaattag     1140
ccgggtgtgg tggcaagcgc ctgtaatccc agctactcgg ttggttgggc aggagaatcg     1200
cttgaacccg ggaggcggag gttgcagtga gccgagatcg cgccattgca ctccagcctg     1260
ggcgacaaga gcgagactct gtctcaaaaa aaaaaaaaaa agaagtagaa gggaagaaaa     1320
tcgcaaggaa ctagactaaa a                                               1341

<210> SEQ ID NO 9
<211> LENGTH: 21
<212> TYPE: DNA
<213> ORGANISM: Artificial Sequence
<220> FEATURE:
<223> OTHER INFORMATION: Primer for LAPTM4B allele genotyping

<400> SEQUENCE: 9
gccgactagg ggactggcgg a                                                 21

<210> SEQ ID NO 10
<211> LENGTH: 21
<212> TYPE: DNA
<213> ORGANISM: Artificial sequence
<220> FEATURE:
<223> OTHER INFORMATION: Primer for LAPTM4B allele genotyping

<400> SEQUENCE: 10
cgagagctcc gagcttctgc c                                                 21

<210> SEQ ID NO 11
<211> LENGTH: 30
<212> TYPE: DNA
<213> ORGANISM: Artificial sequence
<220> FEATURE:
<223> OTHER INFORMATION: Primer for promoter transcriptional activity
      analysis

<400> SEQUENCE: 11
gcgctcgagg ctccaggtgg aagagtgtgc                                        30

<210> SEQ ID NO 12
<211> LENGTH: 30
<212> TYPE: DNA
<213> ORGANISM: Artificial sequence
<220> FEATURE:
<223> OTHER INFORMATION: Primer for promoter transcriptional activity
      analysis
```

<400> SEQUENCE: 12
gcgctcgagt aaaaacgctg tgccaggcgt                                   30

<210> SEQ ID NO 13
<211> LENGTH: 30
<212> TYPE: DNA
<213> ORGANISM: Artificial sequence
<220> FEATURE:
<223> OTHER INFORMATION: Primer for promoter transcriptional activity
      analysis

<400> SEQUENCE: 13
ccgctcgagt accggaagca cagcgaggat                                   30

<210> SEQ ID NO 14
<211> LENGTH: 30
<212> TYPE: DNA
<213> ORGANISM: Artificial sequence
<220> FEATURE:
<223> OTHER INFORMATION: Primer for promoter transcriptional activity
      analysis

<400> SEQUENCE: 14
gcgctcgaga gtagaaggga agaaaatcgc                                   30

<210> SEQ ID NO 15
<211> LENGTH: 29
<212> TYPE: DNA
<213> ORGANISM: Artificial sequence
<220> FEATURE:
<223> OTHER INFORMATION: Primer for promoter transcriptional activity
      analysis

<400> SEQUENCE: 15
gcgaagcttg gacttggcca tgtgacccg                                    29

<210> SEQ ID NO 16
<211> LENGTH: 29
<212> TYPE: DNA
<213> ORGANISM: Artificial sequence
<220> FEATURE:
<223> OTHER INFORMATION: Primer for promoter transcriptional activity
      analysis

<400> SEQUENCE: 16
gcgaagcttg gacttggcca tgtgacccg                                    29

<210> SEQ ID NO 17
<211> LENGTH: 30
<212> TYPE: DNA
<213> ORGANISM: Artificial sequence
<220> FEATURE:
<223> OTHER INFORMATION: Primer for promoter transcriptional activity
      analysis

<400> SEQUENCE: 17
gcgctcgagg ctccaggtgg aagagtgtgc                                   30

<210> SEQ ID NO 18
<211> LENGTH: 30
<212> TYPE: DNA
<213> ORGANISM: Artificial sequence
<220> FEATURE:
<223> OTHER INFORMATION: Primer for promoter transcriptional activity
      analysis

```
<400> SEQUENCE: 18
gcgctcgagt aaaaacgctg tgccaggcgt                                      30

<210> SEQ ID NO 19
<211> LENGTH: 47
<212> TYPE: DNA
<213> ORGANISM: Homo sapiens

<400> SEQUENCE: 19
ttactcaccg ggtgcttgga gctccagcag ctggctggag cccgcga                   47

<210> SEQ ID NO 20
<211> LENGTH: 46
<212> TYPE: DNA
<213> ORGANISM: Homo sapiens

<400> SEQUENCE: 20
gggtgcttgg agctccagca gctgcttgga gctccagcag ctggct                    46
```